United States Patent
Dang et al.

(10) Patent No.: US 9,034,851 B2
(45) Date of Patent: May 19, 2015

(54) SUBSTITUTED PYRIMIDINES

(71) Applicant: MERCK SHARP & DOHME CORP., Rahway, NJ (US)

(72) Inventors: Qun Dang, Westfield, NJ (US); Changyou Zhou, Princeton, NJ (US); Wuxin Zou, Beijing (CN); Yuxia Hua, Beijing (CN)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/346,522

(22) PCT Filed: Sep. 19, 2012

(86) PCT No.: PCT/US2012/055956
§ 371 (c)(1),
(2) Date: Mar. 21, 2014

(87) PCT Pub. No.: WO2013/043621
PCT Pub. Date: Mar. 28, 2013

(65) Prior Publication Data
US 2014/0235583 A1    Aug. 21, 2014

Related U.S. Application Data

(60) Provisional application No. 61/555,685, filed on Nov. 4, 2011.

(30) Foreign Application Priority Data

Sep. 23, 2011   (WO) ................ PCT/CN2011/080117

(51) Int. Cl.
| | | |
|---|---|---|
| C07D 239/28 | (2006.01) |
| C07D 239/36 | (2006.01) |
| A61K 31/505 | (2006.01) |
| A61K 31/506 | (2006.01) |
| C07F 9/6558 | (2006.01) |
| C07D 413/12 | (2006.01) |
| C07D 413/04 | (2006.01) |
| C07F 9/6512 | (2006.01) |

(52) U.S. Cl.
CPC .......... *C07F 9/65583* (2013.01); *C07D 239/36* (2013.01); *C07D 413/12* (2013.01); *C07D 413/04* (2013.01); *C07F 9/65127* (2013.01)

(58) Field of Classification Search
CPC .. C07D 239/28; C07D 239/36; A61K 31/505; A61K 31/506
USPC ............................. 544/243, 319; 514/86, 269
See application file for complete search history.

(56) References Cited

U.S. PATENT DOCUMENTS

| | | |
|---|---|---|
| 7,166,609 B2 | 1/2007 | Klingler et al. |
| 2007/0072876 A1 | 3/2007 | Tadiparthi et al. |
| 2009/0239876 A1 | 9/2009 | Clements et al. |
| 2011/0046132 A1 | 2/2011 | Hocutt et al. |

FOREIGN PATENT DOCUMENTS

| | | | |
|---|---|---|---|
| WO | WO 02/00647 | * | 1/2002 |
| WO | WO2006094292 | | 9/2006 |
| WO | WO2007038571 | | 4/2007 |
| WO | WO2007150011 | | 12/2007 |
| WO | WO2009086044 | | 7/2009 |
| WO | WO2009117269 | | 9/2009 |
| WO | WO2013040790 | | 3/2013 |
| WO | WO2013043624 | | 3/2013 |

OTHER PUBLICATIONS

Mole, David R et al, 2-Oxoglutarate Analogue Inhibitors of HIF Prolyl Hydroxylase, Bioorganic & Medicinal Chemistry Letters, 2003, 2677-2680, 13, Elsevier Ltd., Oxford, UK.

* cited by examiner

Primary Examiner — Deepak Rao
(74) Attorney, Agent, or Firm — Matthew A. Leff; John C. Todaro

(57) ABSTRACT

The present invention relates to substituted pyrimidines useful as HIF prolyl hydroxylase inhibitors to treat anemia and like conditions.

15 Claims, No Drawings

SEQUENCE LISTING

<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: PHD2 Substrate

<400> SEQUENCE: 1

Asp Leu Asp Leu Glu Met Met Leu Ala Pro Tyr Ile Pro Met Asp Asp
 1               5                  10                  15

Asp Phe Gln Leu
            20

SUBSTITUTED PYRIMIDINES

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)-, 2-ketoglutarate- and ascorbate-dependent dioxygenase enzymes called PHD-1 (EGLN2, or egg laying abnormal 9 homolog 2, PHD2 (EGLN1), and PHD3 (EGLN3). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-α hydroxylation reaction is less efficient and HIF-α is available to dimerize with HIF-β. HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desferrioxamine) and analogs of 2-ketoglurate (e.g., N-oxalyl glycine). The compounds of the present invention inhibit the HIF prolyl hydroxylases (PHD-1, PHD-2, PHD-3) and can also serve to modulate HIF levels. These compounds therefore have utility for the treatment and/or prevention of disorders or conditions where HIF modulation is desirable, such as anemia and ischemia. As an alternative to recombinant erythropoietin therapy, the compounds of the present invention provide a simpler and broader method for the management of anemia.

SUMMARY OF THE INVENTION

The present invention concerns compounds of formula I

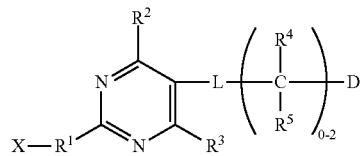

which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides compounds of formula I and pharmaceutically acceptable salts and solvates thereof:

A compound of formula I and pharmaceutically acceptable salts and solvates thereof

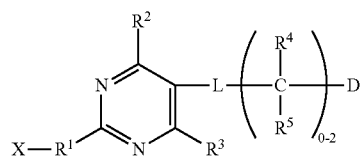

$R^1$ is —$CONR^a(C_{1-2})$alkyl-, a heteroarylene selected from isoxazoldiyl, pyrazoldiyl, imidazoldiyl, oxazoldiyl, thiazoldiyl, pyridindiyl, pyradizindiyl, and pyrimidindiyl;

$R^2$, $R^3$, and $R^6$ are each independently selected from hydrogen, hydroxy, and $C_{1-6}$alkyl;

X is selected from —COOR, —PO(R')OR, —PO(OR)$_2$, —PO(NRR)$_2$, —SO$_3$R, —PO($C_{1-10}$alkyl)OR, PO($C_{3-10}$ cycloalkyl)OR, PO(H)OR, and PO(NHCR'R"COOR)$_2$;

R is independently selected from hydrogen, $C_{1-10}$alkyl, —$C_{1-5}$ alkylaryl, —CR'R'—OCO—$C_{1-10}$alkyl, and CR'R'—OCO—OC$_{1-10}$ alkyl;

R' and $R^{6"}$ are independently selected from hydrogen and $C_{1-10}$ alkyl;

L is selected from CONR$^6$—, and NR$^6$CO—;

D is selected from hydrogen, aryl and heteroaryl;

$R^a$, $R^4$, and $R^5$ are each independently selected from
hydrogen,
halogen,
carboxyl $C_{0-10}$ alkyl,
$C_{1-10}$ alkyl,
$C_{2-10}$ alkenyl,
$C_{2-10}$ alkynyl,
$C_{1-10}$ alkenylamino,
$C_{1-10}$ alkyl(oxy)$_{0-1}$ carbonyl$C_{1-10}$ alkyl,
aryl $C_{0-10}$ alkyl(oxy)$_{0-1}$ carbonyl$C_{1-10}$ alkyl, $C_{3-8}$ cycloalkyl $C_{0-10}$ alkyl(oxy)$_{0-1}$carbonyl $C_{1-10}$ alkyl,
($C_{3-8}$)heterocyclyl $C_{0-10}$ alkyl(oxy)$_{0-1}$carbonyl $C_{1-10}$ alkyl,
($C_{3-8}$)heterocycloalkyl $C_{0-10}$ alkyl(oxy)$_{0-1}$ carbonyl $C_{1-10}$ alkyl,
aryl$C_{0-10}$ alkyl,
$C_{3-8}$ cycloalkyl $C_{0-10}$ alkyl,
$C_{3-8}$ heterocyclyl $C_{0-10}$ alkyl,
$C_{3-8}$ heterocycloalkyl $C_{0-10}$ alkyl,
$C_{1-10}$ alkoxyl, and
hydroxy $C_{0-10}$alkyl;
wherein, $R^1$, $R^a$, $R^4$, $R^5$, and D are optionally substituted with 1, 2, or 3 substituent $R^7$, selected from:
halogen,
(carbonyl)$_{0-1}C_{1-10}$ alkyl,
(carbonyl)$_{0-1}C_{2-10}$alkenyl,
(carbonyl)$_{0-1}C_{2-10}$alkynyl,
$C_{1-10}$ alkylcarbonyl,
$C_{2-10}$ alkenylcarbonyl,
$C_{2-10}$ alkynylcarbonyl,
aryl $C_{0-10}$ alkyl,
($C_{3-8}$)heterocyclyl $C_{0-10}$ alkyl,
$C_{3-8}$ cycloalkyl $C_{0-10}$ alkyl,
($C_{3-8}$)heterocycloalkyl $C_{0-10}$ alkyl,
$C_{1-4}$acylamino $C_{0-10}$ alkyl,
$C_{0-10}$ alkylamino $C_{0-10}$ alkyl,
aryl$C_{0-10}$ alkylamino $C_{0-10}$ alkyl,
$C_{3-8}$ cycloalkyl $C_{0-10}$ alkylamino $C_{0-10}$ alkyl,
$C_{3-8}$ heterocyclyl $C_{0-10}$ alkylamino $C_{0-10}$ alkyl,
$C_{3-8}$ heterocycloalkyl $C_{0-10}$ alkylamino $C_{0-10}$ alkyl,
$C_{1-10}$alkyloxy $C_{0-10}$alkyl,
($C_{1-10}$ alkyl)$_2$aminocarbonyloxy,
hydroxy $C_{0-10}$alkyl,
$C_{1-10}$ alkylsulfonyl,
$C_{1-10}$ alkylsulfonylamino,
aryl $C_{1-10}$ alkylsulfonylamino,
$C_{3-8}$ heterocyclyl $C_{1-10}$ alkylsulfonylamino,
$C_{3-8}$ heterocycloalkyl $C_{1-10}$ alkylsulfonylamino,
$C_{3-8}$ cycloalkyl $C_{1-10}$ alkylsulfonylamino,
cyano,
nitro,
perfluoro$C_{1-6}$alkyl, and
perfluoro$C_{1-6}$alkoxy;
wherein $R^7$ is optionally substituted with 1, 2, or 3 substituents selected from hydrogen, hydroxy, ($C_{1-6}$)alkoxyl, halogen, $CO_2H$, CN, O(C=O)$C_1$-$C_6$ alkyl, $NO_2$, trifluoromethoxy, trifluoroethoxy, —O$_{(0-1)}$($C_{1-10}$)perfluoroalkyl, and $NH_2$; and
provided that when $R^1$ is a heteroarylene, then X is other than —COOR.

Illustrative but nonlimiting examples of compounds of the invention are the following:

1-(5-(benzhydrylcarbamoyl)-4-hydroxypyrimidin-2-yl)-1H-pyrazol-4-yl(methyl)phosphinic acid;
Ethyl N-({5-[(diphenylmethyl)carbamoyl]-4-hydroxypyrimidin-2-yl}carbonyl)-β-alaninate;
Ethyl N-({5-[(diphenylmethyl)carbamoyl]-4-hydroxypyrimidin-2-yl}carbonyl)glycinate;
Methyl N-({5-[(diphenylmethyl)carbamoyl]-4-hydroxypyrimidin-2-yl}carbonyl)glycinate;
2-[({5-[(diphenylmethyl)carbamoyl]-4-hydroxypyrimidin-2-yl}carbonyl)amino]ethanesulfonic acid;
Diethyl {[({5-[(diphenylmethyl)carbamoyl]-4-hydroxypyrimidin-2-yl}carbonyl)amino}methyl]phosphonate;
Ethyl {[({5-[(diphenylmethyl)carbamoyl]-4-hydroxypyrimidin-2-yl}carbonyl)amino]methyl}methylphosphinate;
Benzyl N-({5-[(diphenylmethyl)carbamoyl]-4-hydroxypyrimidin-2-yl}carbonyl)glycinate;
3-(5-(benzhydrylcarbamoyl)-4-hydroxypyrimidine-2-carboxamido)propanoic acid;
2-(5-(benzhydrylcarbamoyl)-4-hydroxypyrimidine-2-carboxamido)acetic acid;
{[({5-[(diphenylmethyl)carbamoyl]-4-hydroxypyrimidin-2-yl}carbonyl)amino]methyl}phosphonic acid;
{[({5-[(diphenylmethyl)carbamoyl]-4-hydroxypyrimidin-2-yl}carbonyl)amino]methyl}methylphosphinic acid;
2-(5-(bis(4-methoxyphenyl)methylcarbamoyl)-4-hydroxy-pyrimidine-2-carboxamido)acetic acid;
Ethyl-2-(5-(bis(4-fluorophenyl)methylcarbamoyl)-4-hydroxypyrimidine-2-carboxamido)acetate;
2-(5-(bis(4-fluorophenyl)methylcarbamoyl)-4-hydroxypyrimidine-2-carboxamido) acetic acid;
Ethyl 2-(4-hydroxy-5-(naphthalen-1-ylmethylcarbamoyl)pyrimidine-2-carboxamido)acetate;
2-(4-hydroxy-5-(naphthalen-1-ylmethylcarbamoyl)pyrimidine-2-carboxamido)acetic acid;
N-({4-hydroxy-5-[(naphthalen-2-ylmethyl)carbamoyl]pyrimidin-2-yl}carbonyl)glycine;
2-(5-(2,2-Diphenylacetamido)-4-hydroxypyrimidine-2-carboxamido)acetic acid;
and pharmaceutically acceptable salts and solvates thereof.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

Unless otherwise specifically noted as only "unsubstituted" or only "substituted", or when substituents are enumerated, alkyl (either as a stand alone radical or as part of a radical such as alkoxy, alkylthio and aralkyl) groups are unsubstituted or substituted with 1 to 3 substituents on each carbon atom, with halo, $C_1$-$C_{20}$ alkyl, $CF_3$, $NH_2$, N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl) C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC (O)NH—, —NH($C_1$-$C_6$ alkyl)NHC(O)—NH($C_1$-$C_6$ alkyl), NHC(O)O$C_1$-$C_6$ alkyl, —NH($C_1$-$C_6$ alkyl)NHSO$_2$($C_1$-$C_6$ alkyl), —($C_0$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

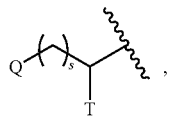

wherein s is an integer equal to zero, 1 or 2, the structure is

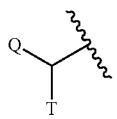

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocyclics in which one ring is a benzene ring and the other ring is saturated or unsaturated, with attachment via any carbon atom that results in a stable compound. Representative examples of this subset include the following:

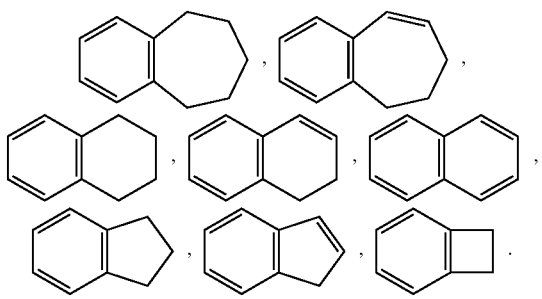

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocyclylic moieties include, but are not limited to, the following: azepanyl, azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazolinyl, isooxazolinyl, oxetanyl, pyranyl, pyrazinyl, pyrazolidinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrahydroisoquinolinyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoauinolinyl, isoquinolinyl, 2,3-dihydrobenzofuryl, 2,3-dihydrobenzo-1,4-dioxinyl (i.e.,

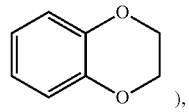), imidazo(2,1-b)(1,3)thiazole, (i.e.,

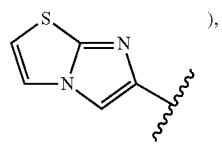), and benzo-1,3-dioxolyl (i.e.,

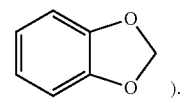).

In certain contexts herein,

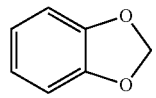

is alternatively referred to as phenyl having as a substituent methylenedioxy attached to two adjacent carbon atoms.

The term "heteroarylene" refers to the diradical group derived from heteroaryl, heterocyclylics, heterocycles, (including substituted heteroaryl, heterocyclylics, heterocycle etc.), as defined above, and are exemplified by the groups pyrazolene, imidazolene, oxazoldylene, thiazoldylene, pyradizindylene, pyrimidinylene, pyridylene, pyridinylene, quinolinylene, benzofuranylene, indolenyl, isoxazolene, and the like.

The terms "arylalkyl" and "alkylaryl" include an alkyl portion where alkyl is as defined above and include an aryl portion where aryl is as defined above. Examples of arylalkyl include, but are not limited to, benzyl, phenylethyl, phenylpropyl, naphthylmethyl, and naphthylethyl. Examples of alkylaryl include, but are not limited to, toluene, ethylbenzene, propylbenzene, methylpyridine, ethylpyridine, propylpyridine and butylpyridine.

Unless otherwise specifically noted as only "unsubstituted" or only "substituted", or when substituents are specifically enumerated, cycloalkyl, aryl (including phenyl) and heterocycle (including heteroaryl) groups are unsubstituted or substituted. As used herein, the terms "substituted $C_3$-$C_{10}$ cycloalkyl", "substituted aryl (including phenyl)" and "substituted heterocycle" are intended to include the cyclic group containing from 1 to 3 substituents in addition to the point of attachment to the rest of the compound. Preferably, the substituents are selected from the group which includes, but are not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)$_2$NC(O)—($C_0$-$C_6$alkyl)O($C_1$-$C_6$ ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

When any variable (e.g., $R^2$, $R^3$, etc.) occurs more than one time in any substituent or in formulas I-III, its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

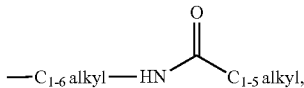

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

In one embodiment of the invention, $R^1$ is —$CONR^a$ ($C_{1-2}$)alkyl-, optionally substituted with 1, 2, or 3 $R^7$ substituents.

In another embodiment of the invention, $R^1$ is a heteroarylene selected from isoxazoldiyl, imidazoldiyl, oxazoldiyl, pyridindiyl, and pyrimidindiyl, optionally substituted with 1, 2, or 3 $R^7$ substituents. In a variant of this embodiment, $R^1$ is selected from isoxazoldiyl optionally substituted with 1, 2, or 3 $R^7$ substituents.

In one embodiment of the invention, $R^2$, $R^3$, and $R^6$ are each independently selected from hydrogen, hydroxy, and $C_{1-4}$alkyl, wherein $R^2$, $R^3$, and $R^6$ are each independently optionally substituted by 1, 2, or 3, $R^7$ substituents.

In one embodiment of the invention, $R^2$ hydroxy, $R^3$ is hydrogen, and $R^6$ is hydrogen.

In one embodiment of the invention, X is selected from —COOR, —PO(R')OR, —PO(OR)$_2$, —SO$_3$R, —PO($C_{1-10}$alkyl)OR, and PO(H)OR.

In one embodiment of the compounds of Formula I, R is independently selected from hydrogen, $C_{1-10}$ alkyl, —$C_{1-5}$ alkylaryl, and —CR'R'—OCO—$C_{1-10}$ alkyl. In a variant of this embodiment, R is independently selected from hydrogen, $C_{1-10}$ alkyl, and —$C_{1-5}$ alkylaryl.

In one embodiment, R' and R" are independently selected from hydrogen and $C_{1-10}$ alkyl.

In one embodiment, L is $CONR^6$. In another embodiment, L is $NR^6CO$—.

In one embodiment, D is selected from hydrogen, aryl, and heteroaryl, optionally substituted by 1, 2, or 3, $R^7$ substituents. In a variant of this invention, D is selected from hydrogen, phenyl and napthalenyl, optionally substituted by 1, 2, or 3, $R^7$ substituents.

In one embodiment, $R^a$, $R^4$, and $R^5$ are each independently selected from hydrogen, aryl$C_{0-10}$ alkyl, $C_{3-8}$ cycloalkyl $C_{0-10}$ alkyl, $C_{3-8}$ heterocyclyl $C_{0-10}$ alkyl, $C_{3-8}$ heterocycloalkyl $C_{0-10}$ alkyl, and hydroxy$C_{0-10}$alkyl; wherein $R^a$, $R^4$, and $R^5$ are each optionally substituted by 1, 2, or 3, $R^7$ substituents.

In an embodiment, $R^a$, $R^4$, and $R^5$ are each independently selected from halogen, aryl $C_{0-10}$ alkyl, ($C_{3-8}$)heterocyclyl $C_{0-10}$ alkyl, $C_{3-8}$ cycloalkyl $C_{0-10}$ alkyl, ($C_{3-8}$)heterocycloalkyl $C_{0-10}$ alkyl, $C_{1-10}$alkyloxy $C_{0-10}$alkyl, hydroxy $C_{0-10}$alkyl, cyano, nitro, perfluoro$C_{1-6}$alkyl, and perfluoro$C_{1-6}$alkoxy; wherein $R^a$, $R^4$, and $R^5$ are each optionally substituted by 1, 2, or 3, $R^7$ substituents.

In one embodiment, wherein $R^a$, $R^4$, and $R^5$ are selected from hydrogen, halogen, and $C_{1-10}$ alkyl.

In another embodiment, $R^a$ is hydrogen, and $R^4$ and $R^5$ are each selected from hydrogen, aryl$C_{0-10}$ alkyl, optionally substituted by 1, 2, or 3, $R^7$ substituents.

In an embodiment of the invention, $R^7$ is selected from halogen, (carbonyl)$_{0-1}C_{1-10}$alkyl, aryl $C_{0-10}$ alkyl, ($C_{3-8}$)heterocyclyl $C_{0-10}$ alkyl, $C_{3-8}$ cycloalkyl $C_{0-10}$ alkyl, ($C_{3-8}$)heterocycloalkyl $C_{0-10}$ alkyl, $C_{1-10}$alkyloxy $C_{0-10}$alkyl, hydroxy $C_{0-10}$alkyl, $C_{1-10}$ alkylsulfonyl, cyano, nitro, perfluoro$C_{1-6}$ alkyl, and perfluoro$C_{1-6}$alkoxy.

In another embodiment, $R^7$ is selected from halogen, (carbonyl)$_{0-1}C_{1-10}$alkyl, $C_{1-10}$alkyloxy $C_{0-10}$alkyl, hydroxy $C_{0-10}$alkyl, cyano, nitro, perfluoro$C_{1-6}$alkyl, and perfluoro $C_{1-6}$alkoxy.

Another embodiment of the invention includes the following compounds:
1-(5-(benzhydrylcarbamoyl)-4-hydroxypyrimidin-2-yl)-1H-pyrazol-4-yl(methyl)phosphinic acid;
Ethyl N-({5-[(diphenylmethyl)carbamoyl]-4-hydroxypyrimidin-2-yl}carbonyl)-β-alaninate;
Ethyl N-({5-[(diphenylmethyl)carbamoyl]-4-hydroxypyrimidin-2-yl}carbonyl)glycinate;
Methyl N-({5-[(diphenylmethyl)carbamoyl]-4-hydroxypyrimidin-2-yl}carbonyl)glycinate;
2-[({5-[(diphenylmethyl)carbamoyl]-4-hydroxypyrimidin-2-yl}carbonyl)amino]ethanesulfonic acid;
Diethyl {[({5-[(diphenylmethyl)carbamoyl]-4-hydroxypyrimidin-2-yl}carbonyl)amino]methyl}phosphonate;
Ethyl {[({5-[(diphenylmethyl)carbamoyl]-4-hydroxypyrimidin-2-yl}carbonyl)amino]methyl}methylphosphinate;
Benzyl N-({5-[(diphenylmethyl)carbamoyl]-4-hydroxypyrimidin-2-yl}carbonyl)glycinate;
3-(5-(benzhydrylcarbamoyl)-4-hydroxypyrimidine-2-carboxamido)propanoic acid;
2-(5-(benzhydrylcarbamoyl)-4-hydroxypyrimidine-2-carboxamido)acetic acid;
{[({5-[(diphenylmethyl)carbamoyl]-4-hydroxypyrimidin-2-yl}carbonyl)amino]methyl}phosphonic acid;
{[({5-[(diphenylmethyl)carbamoyl]-4-hydroxypyrimidin-2-yl}carbonyl)amino]methyl}methylphosphinic acid;
2-(5-(bis(4-methoxyphenyl)methylcarbamoyl)-4-hydroxypyrimidine-2-carboxamido)acetic acid;
Ethyl-2-(5-(bis(4-fluorophenyl)methylcarbamoyl)-4-hydroxypyrimidine-2-carboxamido)acetate;
2-(5-(bis(4-fluorophenyl)methylcarbamoyl)-4-hydroxypyrimidine-2-carboxamido) acetic acid;
Ethyl-2-(4-hydroxy-5-(naphthalen-1-ylmethylcarbamoyl)pyrimidine-2-carboxamido)acetate;
2-(4-hydroxy-5-(naphthalen-1-ylmethylcarbamoyl)pyrimidine-2-carboxamido)acetic acid;
N-({4-hydroxy-5-[(naphthalen-2-ylmethyl)carbamoyl]pyrimidin-2-yl}carbonyl)glycine;
2-(5-(2,2-Diphenylacetamido)-4-hydroxypyrimidine-2-carboxamido)acetic acid;
and pharmaceutically acceptable salts and solvates thereof.

In a variant of this embodiment the compounds of formula 1 include:

1-(5-(benzhydrylcarbamoyl)-4-hydroxypyrimidin-2-yl)-1H-pyrazol-4-yl(methyl)phosphinic acid;
Ethyl N-({5-[(diphenylmethyl)carbamoyl]-4-hydroxypyrimidin-2-yl}carbonyl)-β-alaninate;
Ethyl N-({5-[(diphenylmethyl)carbamoyl]-4-hydroxypyrimidin-2-yl}carbonyl)glycinate;
Methyl N-({5-[(diphenylmethyl)carbamoyl]-4-hydroxypyrimidin-2-yl}carbonyl)glycinate;
2-[({5-[(diphenylmethyl)carbamoyl]-4-hydroxypyrimidin-2-yl}carbonyl)amino]ethanesulfonic acid;
Diethyl {[({5-[(diphenylmethyl)carbamoyl]-4-hydroxypyrimidin-2-yl}carbonyl)amino]methyl}phosphonate;
Ethyl {[({5-[(diphenylmethyl)carbamoyl]-4-hydroxypyrimidin-2-yl}carbonyl)amino]methyl}methylphosphinate;
Benzyl N-({5-[(diphenylmethyl)carbamoyl]-4-hydroxypyrimidin-2-yl}carbonyl)glycinate;
and pharmaceutically acceptable salts and solvates thereof.

One embodiment of the invention includes 2-(5-(bis(4-methoxyphenyl)methylcarbamoyl)-4-hydroxypyrimidine-2-carboxamido)acetic acid; 3-(5-(benzhydrylcarbamoyl)-4-hydroxypyrimidine-2-carboxamido)propanoic acid;
and pharmaceutically acceptable salts and solvates thereof.

Structural representations of compounds having substituents terminating with a methyl group may display the terminal methyl group either using the characters "CH$_3$", e.g. "—CH$_3$" or using a straight line representing the presence of the methyl group, e.g., "—", i.e.,

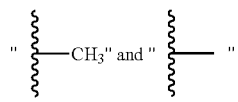

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

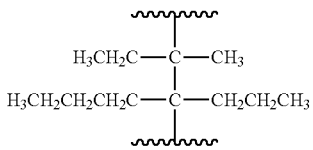

Optical Isomers-Diastereomers-Geometric Isomers-Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts and solvates thereof. Unless specifically mentioned otherwise, reference to one isomer applies to any of the possible isomers. Whenever the isomeric composition is unspecified, all possible isomers are included. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —CH$_2$C(O)— groups (keto forms) may undergo tautomerism to form hydroxyl CH=C(OH)— groups (enol forms). Both keto and enol forms, individually as well as mixtures thereof, are included within the scope of the present invention.

Salts

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. The term "pharmaceutically acceptable salts" refers to salts prepared from pharmaceutically acceptable non-toxic bases or acids. When the compound of the present invention is acidic, its corresponding salt can be conveniently prepared from inorganic bases or organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from organic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methyl-glucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from inorganic or organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methane-sulfonic, mucic, nitric, pamoic, pantothenic, phosphoric, succinic, sulfuric, tartaric, p-toluene-sulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono-, sesqui-, di- and trihydrates.

Prodrugs

The present invention includes within its scope the use of prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIF prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIF prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I.

"Anemia" includes, but is not limited to, chronic kidney disease anemia, chemotherapy-induced anemia (e.g., anemia resulting from antiviral drug regimens for infectious diseases, such as HIV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragés, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other active ingredients known to be useful for improving the level of erythropoietin in a patient.

Abbreviations Used in the Description of the Preparation of the Compounds of the Present Invention AcOH Acetic acid
$Ac_2O$ Acetic anhydride
$Ag_2O$ Silver oxide
aq Aqueous
Bn Benzyl
BnBr benzylbromide
BnCl benzylchloride
BnOH benzylalcohol
brine Saturated aqueous sodium chloride solution
CAN Cerium ammonium nitrate
CDI Carbonyl diimidazole
DBU 1,8-diazabicyclo[5.4.0]undec-7-ene
DEAD diethylazodicarboxylate
DCM Dichloromethane
DIPEA N,N-diisopropylethylaime
DMAP 4-N,N-dimethylaminopyridine
DMF N,N-dimethylformamide
DMSO Dimethyl sulfoxide
DPPA Diphenyl phosphoryl azide
EDC or EDCI 1-(3-dimethylaminopropyl)-3-ethylcarboiimide hydrogenchloride salt
EtOAc or EA Ethyl acetate
Et (et) Ethyl
EtOH Ethanol
$Et_2O$ or ether Diethyl ether
$Et_3N$ triethylamine
g Grams
h or hr Hour
HATU O-(7-Azabenzotriazol-1-yl)-N,N,N',N'-tetramethyluronium hexafluorophosphate
HCl Hydrochloric acid
HOBt 1-hydroxybenzatriazole
HPLC High-performance liquid chromatography
i-PrOH or IPA Isopropyl alcohol
$K_2CO_3$ Potassium carbonate
KOH Potassium hydroxide
LiOH Lithium hydroxide
mg Milligrams
mL Milliliters
mmol Millimole
MeOH Methanol
min Minutes
ms or MS Mass spectrum
μg Microgram(s)
μL Microliters
NaOEt Sodium ethoxide
NaOMe Sodium methoxide
$Na_2SO_4$ Sodium sulfate
NCS N-chlorosuccinimide
NHAc Acetamido
NHCbz Benzyloxycarboxamido
NaOH Sodium hydroxide
$NaN_3$ Sodium azide
$NH_4OH$ ammonium hydroxide
Pd/C Palladium on carbon
$PdCl_2$(dppf) [1,1'-Bis(diphenylphosphino)ferrocene]dichloropalladium(II)
$Pd(OH)_2$ Palladium hydroxide
PG Protecting group
Ph Phenyl group
$PPh_3$ Triphenyphosphine
Rt Retention time
Rt Room temperature
TEA Triethylamine
TFA Trifluoroacetic acid
THF Tetrahydrofuran
$TMSCHN_2$ (trimethylsilyl)diazomethane
TBTU O-(Benzotriazol-1-yl)-N,N,N',N'-tetramethyluronium tetrafluoroborate Synthesis The compounds of this invention may be prepared by employing reactions as shown in the following schemes, in addition to other manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

The following schemes and descriptions illustrate methods which may be employed for the synthesis of the novel compounds described in this invention. All substituents are as defined above unless indicated otherwise. Several strategies based upon synthetic transformations known in the literature of organic synthesis may be employed for the preparation of the title compounds of general formula I. The choice of the method employed is influenced by the selection of the desired substituent groups ($R^1$ through $R^3$, L, X and A) in the title compounds of general formula I.

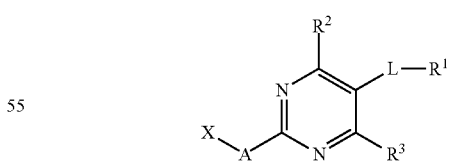

Pyrimidine intermediates useful for the preparation of compounds of formula I of the present invention are either purchased or prepared using suitable procedures reported in the literature (sometimes with minor modifications). One generally useful method for the synthesis of pyrimidines suitable for the preparation of the title compounds of general formula I wherein the substituent $R^2$ is a hydroxy group is illustrated in Scheme 1.

Scheme 1

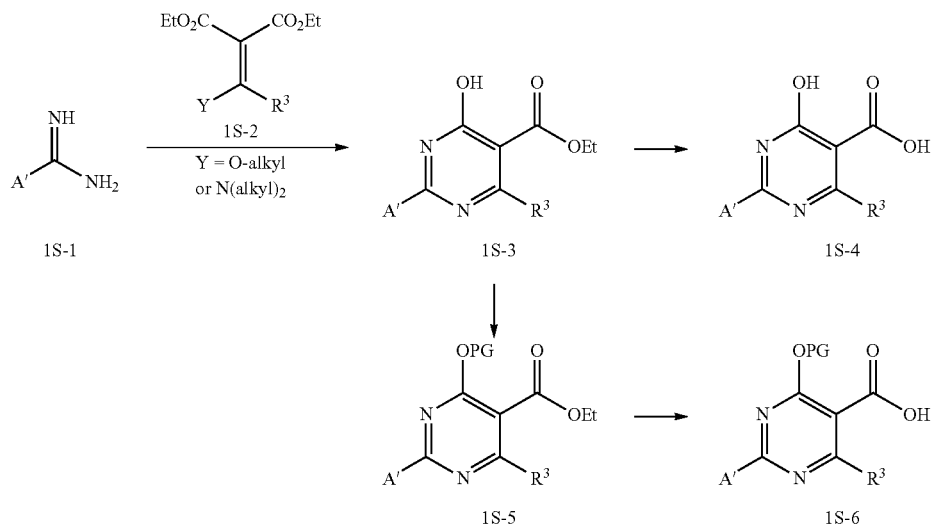

This method involves the initial synthesis of substituted 4-hydroxypyrimidine-5-carboxylates of general formula 1S-4 and 1S-6. The synthesis of 4-hydroxypyrimidine-5-carboxylates exemplified in Scheme 1 is based upon reported methods (Dostert, P.; Imbert, T.; Ancher, J. F.; Langlois, M.; Bucher, B.; Mocquet, G. *Eur. J. Med. Chem.* 1982, 17, 437-44. Juby, P. F.; Hudyma, T. W.; Brown, M.; Essery, J. M.; Partyka, R. A. *J. Med. Chem.* 1979, 22, 263-9).

In some instances A' group may be the desired X-A-group for compounds of formula I, if the synthetic sequence permits, while in other cases A' group could be derivatized at a suitable stage of the synthetic sequence so that a desired X-A-group can be obtained for the final compounds of formula I. The same strategy applies to $R^3$ groups as well.

In this method, an amidine or a suitable salt thereof of general formula 1S-1 is reacted with an optionally substituted diethyl methylenemalonate of general formula 1S-2. This reaction is usually conducted using a suitable base such as sodium or potassium ethoxide in ethanol, although other reaction conditions may also be applied. The alkoxide base and the alcohol solvent are chosen to correspond to the esters present in reagent 1S-2 to prevent the formation of mixtures of esters in the product of general formula 1S-3. When required, the reaction is conducted at elevated temperature, typically at the reflux temperature of the solvent until reaction is complete (generally within 1-4 hours). It is also convenient to conduct this reaction under microwave heating in sealed reaction vessels. In this instance, the reaction is generally conducted at temperatures between 80 and 120° C. and the reactions are typically completed in 5-30 minutes.

Compounds of general formula 1S-3 are useful intermediates to prepare compounds of formula I of the present invention. For example, compounds of general formula 1S-3 may be hydrolyzed using a suitable base (e.g. sodium or potassium hydroxide) to give acids of formula 1S-4; alternatively, they are converted to compounds of formula 1S-5, in which the hydroxy group of the pyrimidine core is protected with a desired protecting group (e.g. the protecting group is benzyl, para-methoxybenzyl, trityl, or tert-butyl-dimethyl silyl). Hydrolysis of compounds of formula 1S-5 gives acids of general formula 1S-6, which is readily achieved under suitable ester hydrolysis reaction conditions (Wuts, P. G. M.; Greene, T. W., Protecting Groups in Organic Synthesis, John Wiley and Sons, 4$^{th}$ Edition, 2007).

When amidines of general formula 1S-1 are not commercially available, they may be prepared by a variety of methods known in the literature. Amidines are commonly prepared from nitriles using the Pinner reaction and variations thereof (see Amidines and N-substituted amidines. Dunn, Peter J. in Comprehensive Organic Functional Group Transformations 1995, 5, 741-82, 1161-308 Editor(s): Katrizky, Alan R.; Meth-Cohn, Otto; Rees, Charles Wayne. Publisher: Elsevier, Oxford, UK). Amidines may also be prepared from esters using the method reported by Gielen et al. (Gielen, H.; Alonso-Alija, C.; Hendrix, M.; Niewohner, U.; Schauss, D. *Tetrahedron Lett.* 2002, 43, 419-21).

In instances where the substituent A is selected to be a five-membered heterocyclic ring, it is possible that this heterocyclic group be bonded to the carbon atom at the 2-position of the pyrimidine ring through either a carbon-carbon or a carbon-nitrogen bond. In the case of attachment through a carbon-carbon bond, the precursor for the substituent A is an amidine of general formula 1S-1 and the method using 1S-1 for the synthesis of the title compound of general formula I is as described in the preceding reaction schemes.

When a substituent A is attached through a carbon-nitrogen bond, the precursor for the substituent A is a guanidine of general formula 2S-7. In this example, the synthesis begins with the condensation of the guanidine derivative of general formula 2S-7 with compounds of general formula 2S-8 (or a diethyl ethoxymethylenemalonate of general formula 1S-2 when it is desired that $R^2$=OH) to afford the substituted pyrimidine-5-carboxylate derivative of general formula 2S-9. Ester hydrolysis as described above affords compounds of formula 2S-10, which is useful to prepare compounds of general formula I wherein the group A is a five-membered heterocyclic group attached to the pyrimidine 2-position with a carbon-nitrogen bond.

Scheme 2

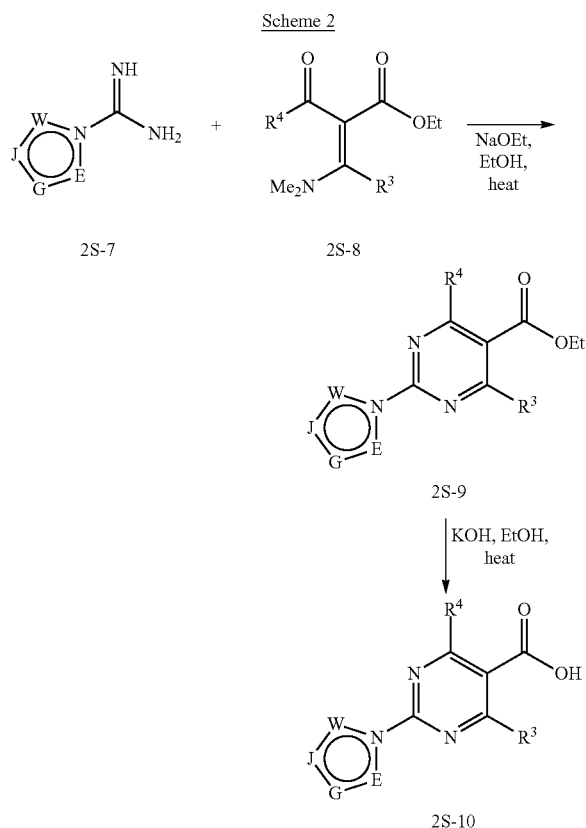

Scheme 3

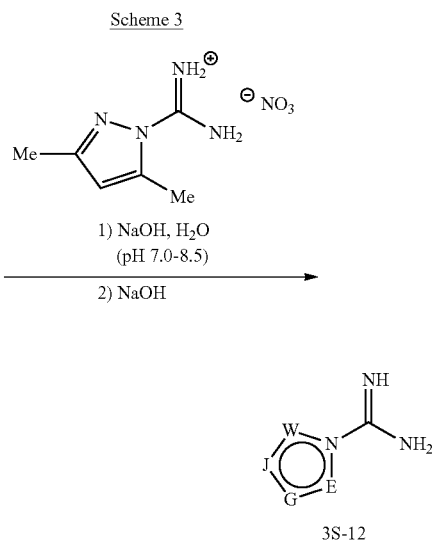

In cases when the guanidine derivative (2S-7) bearing the desired substituents is not commercially available, it may be synthesized using reported methods for guanidine synthesis (e.g. the guanidinylation of amines). Numerous methods for the guanidinylation of amines are reported (see Katritzky, A. R.; Rogovoy, B. V. ARKIVOC 2005, 4, 49-87; http://www.arkat-usa.org/ark/journal/2005/I04_Zefirov/1256/1256.pdf). One general method is shown in Scheme 3, which entails the reaction of compounds of formula 3S-11 with 3,5-dimethyl-1-pyrazolylformamidinium nitrate to afford a guanidine of general formula 3S-12 using the method described by Fletcher et al. (Fletcher, D J.; Ganellin, C. R.; Piergentili, A.; Dunn, P. M.; Jenkinson, D. H. *Bioorg. Med. Chem.* 2007, 15, 5457-79).

It is recognized that the title compounds of general formula I prepared as described above may be further modified using known methods and that the starting materials selected for use in the reaction schemes above may contain functional groups to enable said further transformation. For instance, aromatic rings in the title compounds of general formula I may be subjected to a variety of aromatic substitution reactions such as nitration, halogenation and the like. Aromatic substituent groups in the title compounds of general formula I bearing leaving groups such as halogens, triflates or the like, can be employed in a variety of metal-catalyzed cross coupling reactions to incorporate new substitution patterns. For example, palladium-catalyzed cross coupling reactions such as those described by Suzuki, Stille, Buchwald and others, may be used to introduce a variety of new substituent groups. Substituent groups that may be introduced using such cross-coupling methods include, but are not limited to, alkyl, alkenyl, alkynyl and aryl groups as well as acyl groups (e.g. carboxylic acids, esters, amides, or ketones), hydroxy and amino or substituted amino groups.

Other pyrimidines with various substituents at the 5-position (wherein R" is not a carboxylate) are also prepared via cyclization reactions similarly as reactions described in Schemes 1 & 2, which are exemplified in Scheme 4.

Scheme 4

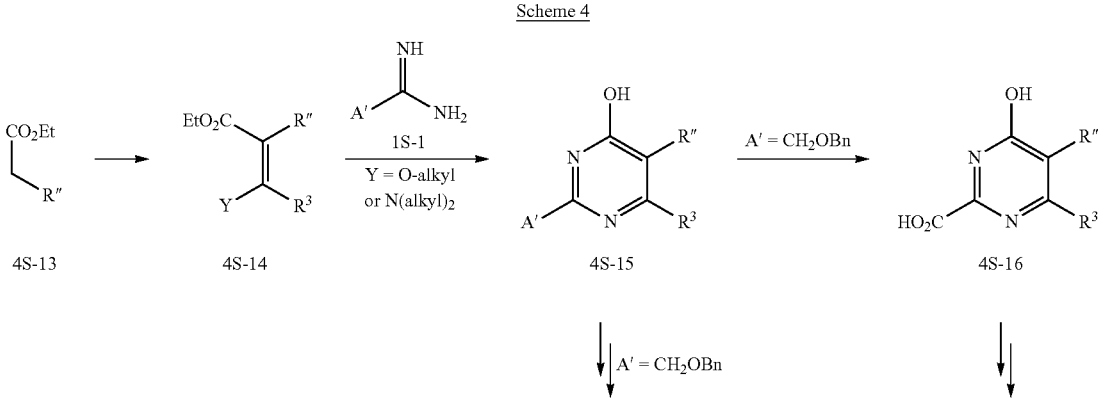

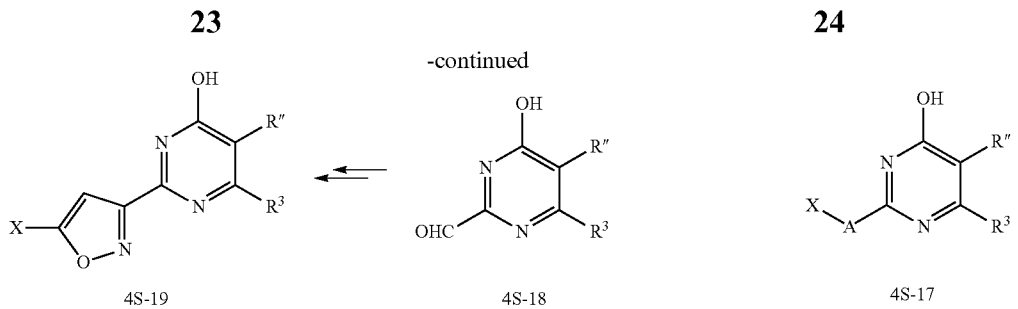

In some instances A' group may be the desired X-A-group for compounds of formula I, if the synthetic sequence permits, while in other cases A' group could be derivatized at a suitable stage of the synthetic sequence so that a desired X-A-group can be obtained for the final compounds of formula I. The same strategy applies to $R^3$ groups as well.

For example, compounds of formula 4S-15 are prepared when amidines 1S-1 are cyclized with esters 4S-14 wherein X=O-alkyl under reaction conditions exemplified as in Scheme 1. Alternatively, compounds of formula 4S-14 wherein X=N(alkyl)$_2$ are also cyclized with amidines 1S-1 to give compounds of formula 4S-15 (Chen, W.; Feng, J.; Tu, H. Huaxue Tongbao, 2006, 69, 623-6). The esters 4S-14 can be prepared by reaction of esters 4S-13 with a substituted carboxamide dimethyl acetal.

When A' is CH$_2$OBn, then compounds 4S-15 are particularly useful intermediates to prepare compounds of formula I wherein A groups are amides and heterocycles. For example, removal of the Bn protecting group using a suitable method (e.g. under hydrogenation conditions) followed by appropriate oxidation reactions (e.g. Dess-Martin oxidation) produce compounds 4S-18; the aldehyde group of compounds 4S-18 is useful to install other desired X-A groups. For example, conversion of the aldehyde in compounds 4S-18 to oxime followed by a [3+2] cycloaddition reaction (via the chlorooxime) give compounds 4S-19 which is useful to prepare compounds of formula I wherein A group is an isoxazolyl group. Alternatively, oxidation of the aldehyde group in compounds 4S-18 to its corresponding carboxylic acid using a suitable oxidation reaction (e.g. NaClO$_2$) and followed by suitable amide bond formation reactions (e.g. TBTU coupling) produce compounds 4S-17, which is useful to prepare compounds of formula I wherein A is an amide group.

In some instances R" groups in compounds exemplified in Scheme 4 may already have the desired L-R$^1$ moieties, while in other cases the desired L-R$^1$ could be introduced by modifications of R" using literature reported procedures with suitable optimizations.

The methods presented in reaction Schemes 1 and 2 may be further generalized when it is desired to prepare compounds of general formula I where neither of the $R^2$ or $R^3$ substituents are hydroxy groups.

Scheme 5

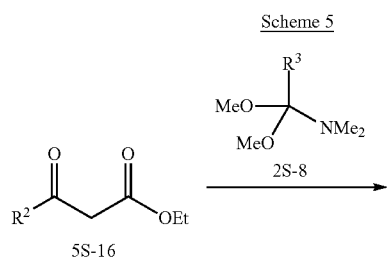

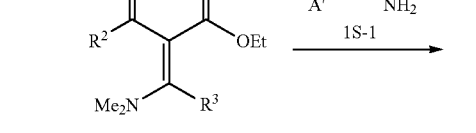

Reaction Scheme 5 illustrates the process beginning with a beta-ketoester of general formula 5S-16 bearing the $R^2$ substituent. The ester of general formula 5S-16 is condensed with a carboxamide dimethyl acetal of general formula 2S-8 to afford the vinylogous amide of general formula 5S-17. The intermediate 5S-17 is then reacted with an amidine derivative of general formula 1S-1 using the method of Schenone et al. (Schenone, P.; Sansebastiano, L.; Mosti, L. J. Heterocyclic Chem. 1990, 27, 295) to afford the alkyl pyrimidine-5-carboxylate of general formula 5S-18. Hydrolysis of compounds of formula 5S-18 under suitable conditions (e.g. KOH or NaOH in EtOH—H$_2$O, heating when necessary) produces compounds of formula 5S-19. The compounds of general formula 5S-19 are then converted to the title compounds of general formula I using the methods described previously.

In one aspect, compounds of formula I are prepared via pyrimidine ring formation reactions (e.g. Schemes 1, 2, 4, 5) with the desired substituents (e.g. X, A, $R^2$, $R^3$ and L) at various positions. In another aspect, the desired substituents on the pyrimidine core can be introduced after the pyrimidine ring is formed, which can be achieved using synthetic methods reported in the literature. For example, the hydroxy group present at the pyrimidine 4-position in compounds of general formulae 1S-3, 1S-4, or 4S-15 may be converted to a halogen substituent upon reaction with a suitable halogenating reagent (e.g. POCl$_3$, BB$_{r3}$, etc.).

Compounds of general formula I wherein L is an amino or an amino derivative can be prepared from suitable pyrimidine derivatives such as 1S-4, 1S-6, 2S-10 and 5S-19 using synthetic methods reported in the literature. For example, carboxylic acids of formula 5S-19 are converted to their corresponding amines of formula 6S-20 using suitable methods such as Curtis rearrangement reactions, Scheme 6. The amino group in compounds of formula 6S-20 is further derivatized using common synthetic methods such as amide bond formation reactions (e.g. CDI couplings, EDCI couplings, reactions with acyl chlorides, etc.), sulfonamide bond formation reactions (e.g. reactions with sulfonyl chlorides in the presence of a suitable base), reductive amination reactions with a suitable carbonyl compounds (e.g. aldehydes and ketones). For example, compounds of formula I wherein L is NHCO— and/or NHSO$_2$— are prepared from compounds of formula 6S-20 as depicted in Scheme 6. In another aspect, carboxylic acids such as compounds of formula 5S-19 can be converted to their corresponding acyl azide such as compounds of formula 6S-22, and under suitable thermal rearrangement reaction conditions acyl azides such as 6S-22 can be converted to their corresponding isocyanate, and subsequent reactions of the resulting isocyanate with various nucleophiles such as alcohols, amines and thiols can produce compounds of formula 6S-23 wherein L is a carbamate (—NHCOO—), urea (—NHCONH—), or thiocarbamate (—NHCOS—). (March's advanced organic chemistry, Wiley-interscience, 2007; Comprehensive Organic Transformations: a guide to functional group preparations by Richard Larock, Wiley-VCH, 2000)

as compounds 6S-23 and 6S-21. Alternatively, the X moiety could be brought in during the pyrimidine formation reaction. X groups may be introduced via organometallic chemistry, for example a metal-anion could be generated from an aryl halide (such as aryl bromide or aryl iodide), and subsequent reaction of the anion with a suitable electrophile such as alkyl chloroformate, dialkyl chlorophosphate and final deprotection reaction such as base hydrolysis or TMSBr-mediated ester removal reactions, leading to compounds of formula I where X is a COOH, or PO(OH)$_2$, or —PO(alkyl)(OH) groups. Representative examples are shown in Scheme 7 for compounds of formula I where in A group is a pyrazolyl group and X is a methylphosphinic acid group or a carboxylic

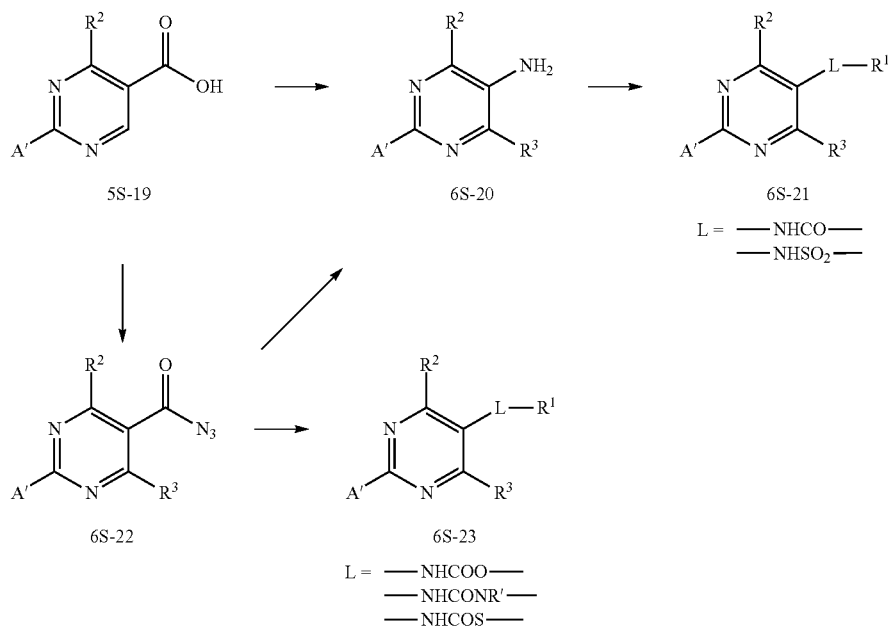

X moiety associated with the compounds of formula I could be introduced once the pyrimidine ring is formed such acid group, however methods to prepare compounds of formula I are not limited to examples shown in the schemes.

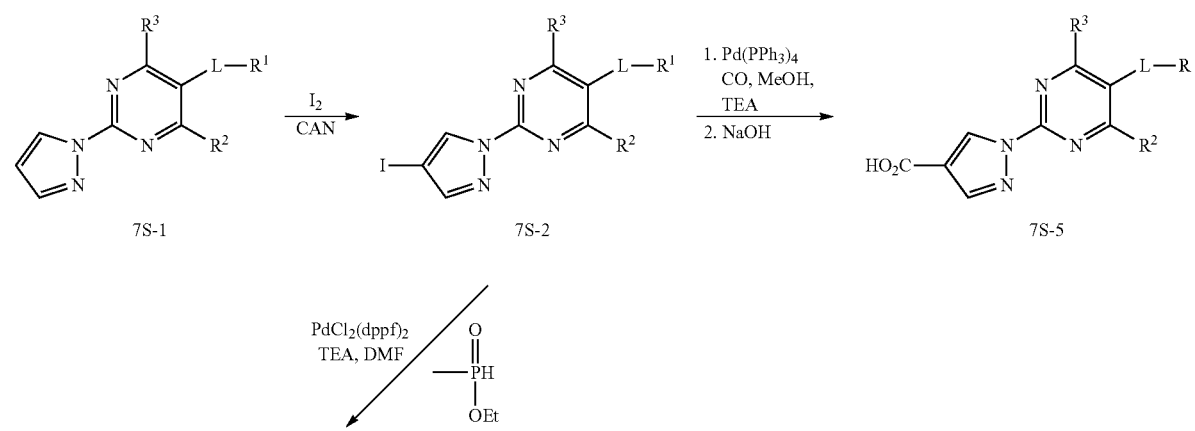

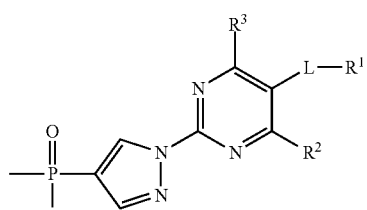

7S-3

NaOH →

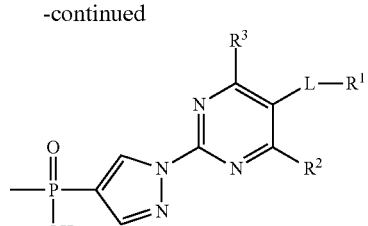

7S-4

The halogenation of the pyrazolyl group is readily achieved using literature reported procedures, for example iodination of compounds of formula 7S-1 was carried out using iodine and CAN to give compounds 7S-2. Phosphorylation of aryl halides such as compounds 7S-2 can be carried out using a suitable phosphite in the presence of a suitable transition metal catalyst. For example, treatment of compounds 7S-2 with ethyl methylphosphite and $PdCl_2(dppf)_2$ in DMF gave compounds 7S-3. Phosphinate and phosphonate esters are converted to their corresponding acids using various deprotection reactions. For example, treatment of compounds 7S-3 with sodium hydroxide under suitable conditions gave compounds 7S-4. Alternatively, halo-substituted compounds such as 7S-2 are useful to prepare compounds of formula I wherein X is other groups such as COOH. Thus, carbonylation of compounds 7S-2 under transition metal catalyzed conditions (e.g. $Pd(PPh_3)_4$) produce the corresponding carboxylate ester and subsequent hydrolysis (e.g. using NaOH) give compounds 7S-5.

General Methods

Reactions sensitive to moisture or air were performed under nitrogen using anhydrous solvents and reagents. The progress of reactions was determined by either analytical thin layer chromatography (TLC) performed with E. Merck pre-coated TLC plates, silica gel 60F-254, layer thickness 0.25 mm or liquid chromatography-mass spectrum (LC-MS).

Analytical HPLC/MS—Standard Method:

Mass analysis was performed on a Waters Micromass® ZQ™ with electrospray ionization in positive ion detection mode.

High Performance Liquid Chromatography (HPLC)

HPLC using an acidic buffer system was conducted on an Agilent 1100 series HPLC on Waters C18 XTerra 3.5 μm 3.0×50 mm column with gradient 10:90-100 v/v $CH_3CN/H_2O$+v 0.05% TFA over 3.75 min then held at 100 $CH_3CN$+v 0.05 TFA for 1.75 min; flow rate 1.0 mL/min, UV wavelength 254 nm (all HPLC/MS data was generated with this method unless indicated otherwise).

Analytical HPLC/MS using a basic buffer system: Mass analysis was performed on a Waters Micromass® ZQ™ with electrospray ionization in positive ion detection mode. High performance liquid chromatography (HPLC) was conducted on an Agilent 1100 series HPLC on Waters C18 XBridge 3.5 μm 3.0×50 mm column with gradient 10:90-98:2 v/v $CH_3CN/H_2O$+v 0.025% $NH_4OH$ over 3.25 min then hold at 98:2 $CH_3CN$+v 0.025% $NH_4OH$ for 2.25 min; flow rate 1.0 mL/min, UV wavelength 254 nm.

Concentration of solutions was carried out on a rotary evaporator under reduced pressure. Flash chromatography was performed using a Biotage Horizon or SP1 Flash Chromatography apparatus (Dyax Corp.) on silica gel (32-63 μM particle size, KP-Sil 60 Å packing material type) in pre-packed cartridges or using an ISCO CombiFlash™ Sq 16× or CombiFlash® Companion™ apparatus on silica gel (32-63 μM, 60 Å) in pre-packed cartridges. Microwave reactions were carried out on a Biotage Initiator™ 2.0 or CEM Discover™ system.

Preparative HPLC/MS Standard Method (Using an Acidic Buffer System)

Mass analysis was performed on a Waters Micromass® ZQ™ with electrospray ionization in positive ion detection mode. High performance liquid chromatography (HPLC) was conducted on a Waters Prep. HPLC System on Waters C18 Sunfire 5 μm 30×100 mm column with gradient 10:90-100 v/v $CH_3CN/H_2O$+v 0.1% TFA over 12 min; flow rate 50 mL/min, UV wavelength 210-400 nm.

Preparative HPLC/MS Non-Polar Method

Mass analysis was performed on a Waters Micromass® ZQ™ with electrospray ionization in positive ion detection mode. High performance liquid chromatography (HPLC) was conducted on a Waters Prep. HPLC System on Waters C18 Sunfire 5 μm 30×100 mm column with gradient 40:60-100 v/v $CH_3CN/H_2O$+v 0.1% TFA over 10 min then hold at 100 $CH_3CN$+v 0.1% TFA for 4 min; flow rate 50 mL/min, UV wavelength 210-400 nm.

Preparative HPLC/MS Using a Basic Buffer System

Mass analysis was performed on a Waters Micromass® ZQ™ with electrospray ionization in positive ion detection mode. High performance liquid chromatography (HPLC) was conducted on a Waters Prep. HPLC System on Waters C18 XBridge 5 pin 50×150 mm column with gradient 10:90-35:65 v/v $CH_3CN/H_2O$ (pH=10 with $NH_4OH$) over 10 min; flow rate 120 mL/min, UV wavelength 210-400 nm.

Example 1

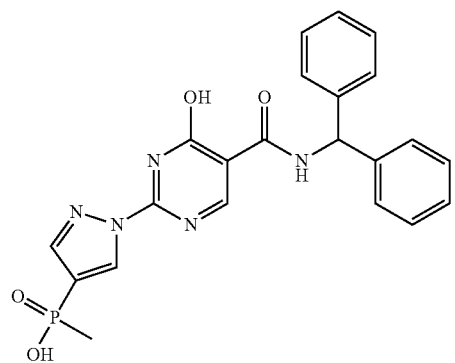

1-1

1-(5-(benzhydrylcarbamoyl)-4-hydroxypyrimidin-2-yl)-1H-pyrazol-4-yl(methyl)phosphinic acid (1-1)

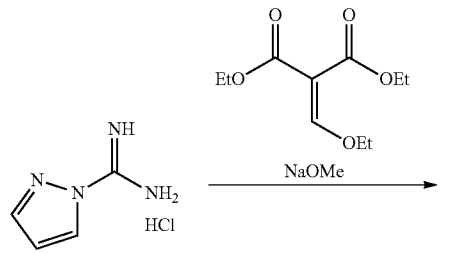

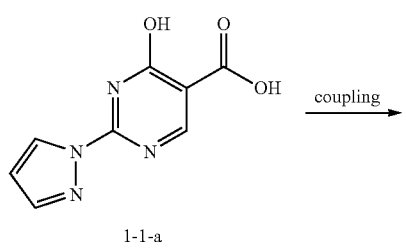

1-1-a

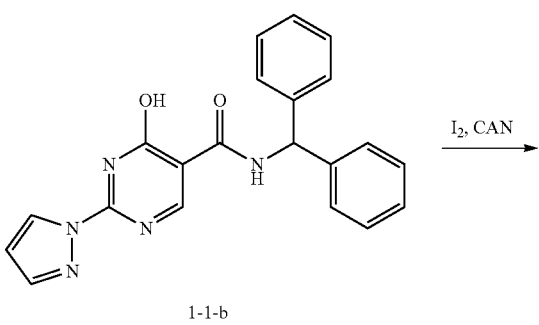

1-1-b

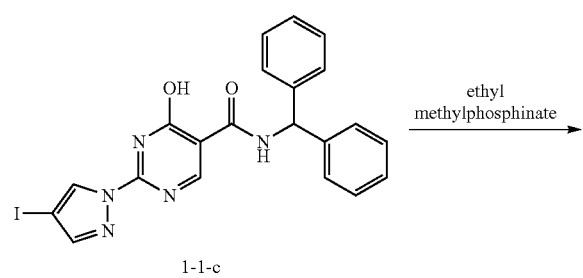

1-1-c

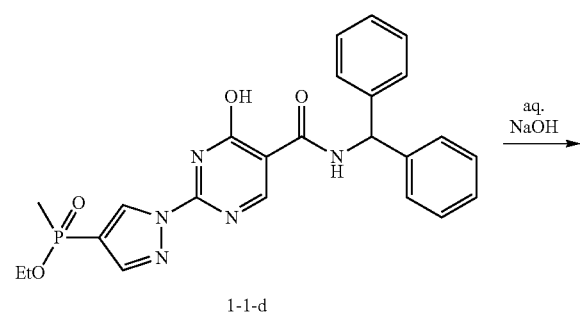

1-1-d

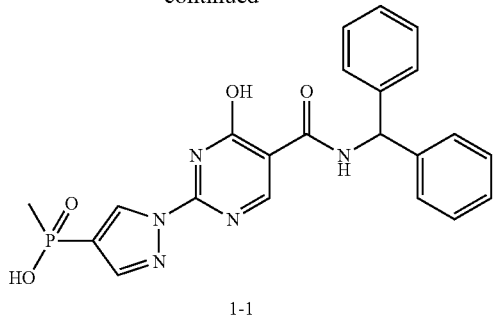

1-1

Step A: 4-Hydroxy-2-(1H-pyrazol-1-yl)pyrimidine-5-carboxylic acid (1-1-a)

To 1H-pyrazole-1-carboximidamide hydrochloride (44.22 g, 299 mmol) in EtOH (500 mL) was added sodium methoxide (102 mL, 448 mmol, 25 wt % in MeOH) and diethyl ethoxymethylenemalonate (61.0 mL, 299 mmol, 99%). The reaction was heated for about 40 min at 75° C. and then cooled slightly (71° C.) before adding potassium hydroxide (33.5 g, 597) in water (125 mL). The reaction was heated to 75° C. for 1 h. During this time an additional portion of EtOH (100 mL) was added to improve mixing. The reaction was cooled to 40° C. before adding aq. HCl (81.3 mL, 991 mmol, 37%) in portions. The reaction aged for 1 h 40 min and then $Et_2O$ (180 mL) was added. The solids were filtered and rinsed with EtOH, $Et_2O$ and then hexane. The solid was then suspended in aq. HCl (300 mL, 0.67 M), filtered and washed with aq. HCl (300 mL, 1 M), 2:1 $Et_2O$:EtOH (350 mL), 1:1 $Et_2O$:EtOH (200 mL), $Et_2O$ (150 mL) and hexane (150 mL) to afford the title compound. HPLC/MS: 207.2 (M+1); Rt=0.61 min.

Step B: N-benzhydryl-4-hydroxy-2-(1H-pyrazol-1-yl)pyrimidine-5-carboxamide (1-1-b)

4-Hydroxy-2-(1H-pyrazol-1-yl)pyrimidine-5-carboxylic acid (1-1-a, 8 g, 38.8 mmol) and CDI (7.24 g, 44.6 mmol) was dissolved in DMF (80 mL), stirred for 45 min at 105° C., then cooled to 77° C. Diphenylmethanamine (9.2 g, 50.4 mmol) and $Et_3N$ (5.41 ml, 38.8 mmol) were then added to the solution at 77° C. and the reaction mixture was stirred for 5 h. The resulting mixture was cooled to ambient temperature, diluted with 150 ml of water, extracted with ethyl acetate (3 times 150 ml). The organic phases were combined, washed with brine, dried over anhydrous $Na_2SO_4$, purified by recrystillized in EtOH/$Et_2O$ (1/10). A yellow solid was obtained as product, 1-1-b, (6.4 g, 45%). $^1$H NMR (300 MHz, DMSO-$d_6$) δ 6.32-6.34 (d, J=8.4, 1H), 6.50-6.51 (m, 1H), 7.29-7.43 (m, 11H), 7.74 (s, 1H), 8.55-8.58 (m, 2H), 11.77 (s, 1H). LC-MS 372 [MH]$^+$.

Step C: N-benzhydryl-4-hydroxy-2-(4-iodo-1H-pyrazol-1-yl)pyrimidine-5-carboxamide (1-1-c)

The product of step B, compound 1-1-b, (3.2 g, 8.6 mmol) was dissolved in acetonitrile (100 mL), and treated with CAN (6.62 g, 12.1 mmol) and $I_2$ (1.42 g, 5.6 mmol). The reaction mixture was stirred for 16 h at 85° C. The resulting mixture was concentrated, diluted with 50 mL of water, stirred for 20 min and filtered. The solid filtrate was dried under vacuum to provide the product, 1-1-c (3.6 g, 84%). $^1$H NMR (300 MHz, DMSO-d$_6$) δ 6.22-6.24 (d, J=6.6, 1H), 7.22-7.39 (m, 11H), 7.55-7.74 (m, 1H), 8.07 (m, 1H), 8.47 (m, 1H), 8.71 (s, 1H), 10.49 (s, 1H). LC-MS 498[MH]$^+$.

Step D: Ethyl 1-(5-(benzhydrylcarbamoyl)-4-hydroxypyrimidin-2-yl)-1H-pyrazol-4-yl(methyl)phosphinate (1-1-d)

To a mixture of product of step C, compound 1-1-c, (1.2 g, 2.4 mmol), ethyl methyl-phosphite (522 mg, 4.8 mmol) and Et$_3$N (610 mg, 6 mmol) in DMF (20 mL) was added PdCl$_2$(dppf) (176 mg). The mixture was allowed to stir overnight at 80° C. The mixture was cooled to room temperature and diluted with water. The resulting mixture was then filtered and the filtrate was extracted with dichloromethane/methanol (5/1). The organic layer was dried over sodium sulfate and concentrated under vacuum. And the residue was purified over silica gel (dichloromethane:methanol=3/1) to provide the product, 1-1-d, (500 mg, 44%).

Step E: 1-(5-(benzhydrylcarbamoyl)-4-hydroxypyrimidin-2-yl)-1H-pyrazol-4-yl(methyl)phosphinic acid (1-1)

The product of step D, 1-1-d, (500 mg, 1.05 mmol) was dissolved in 10 mL of dioxane and treated with 2 mL of 5N NaOH. The mixture was heated at 80° C. for 30 min. The mixture was then diluted with water and extracted with dichloromethane. The aqueous layer was adjusted to pH=5 with AcOH and evaporated to dryness. The residue was used for prep-HPLC to afford the product, 1-1, (130 mg, 28%). $^1$H NMR (300 MHz, DMSO-d$_6$): δ 10.38 (br, 1H), 8.79 (s, 1H), 8.48 (s, 1H), 8.18 (s, 1H), 7.37 (m, 10H), 6.29 (d, 1H), 1.63 (d, 3H). (M+H)$^+$ =450.1.

Example 2

Synthesis of Common Intermediate 2-i

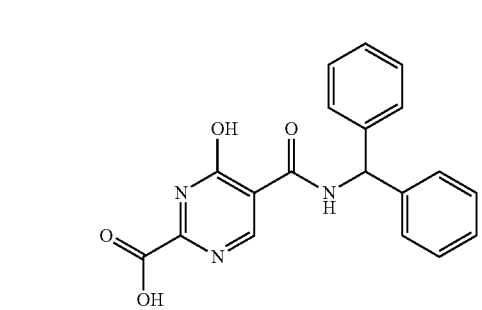

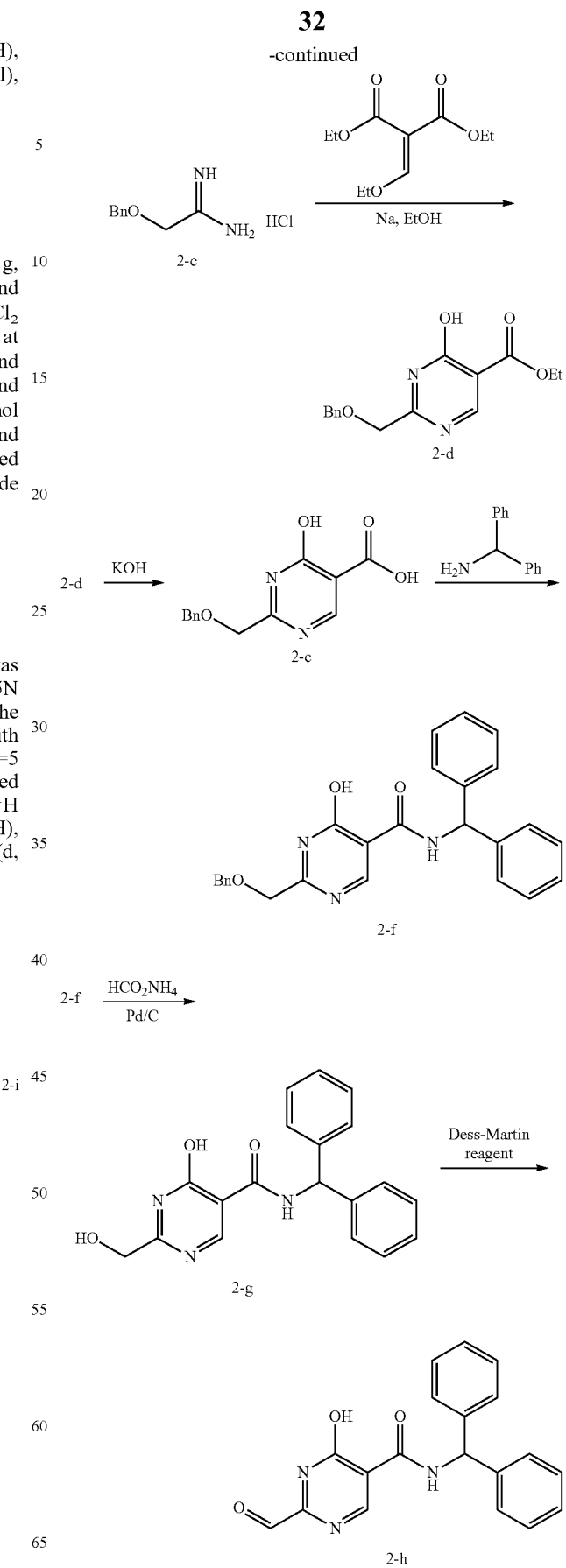

-continued

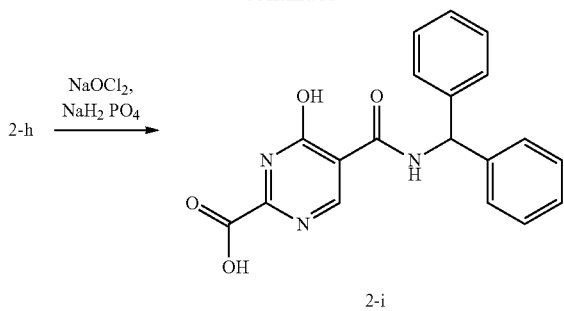 [SMILES: O=C(O)c1ncc(C(=O)NC(c2ccccc2)c2ccccc2)c(O)n1]

The intermediate, 2-i, is utilized in the synthesis of Compounds 2-1 through 2-10, presented below.

Step A: 2-(benzyloxy)acetonitrile (2-i)

A mixture of NaH (4.45 g, 0.13 mol) in anhydrous THF (100 mL) was cooled to 0° C. and treated with a solution of benzyl alcohol (12.98 g, 0.12 mol) in anhydrous THF (300 mL) dropwisely. The resulting mixture was stirred at the ambient temperature for 5 h, and then cooled to 0° C., and treated with a solution of bromoacetonitrile (14.40 g, 0.12 mol) in anhydrous THF (15 mL) dropwisely. The resulting reaction mixture was stirred at the ambient temperature overnight. The reaction mixture was quenched with MeOH (50 mL) and the resulted mixture was filtered through silica gel column, and subsequently evaporated under reduced pressure to obtain compound 2-b (14.0 g) as crude. This crude was directly used next step without further purification.

Step B: 2-(benzyloxy)acetamidine (2-c)

MeONa (0.51 g, 9.5 mmol) was added to a stirred solution of step A product, 2-b (14.0 g, 95 mmol) in methanol (100 mL) at room temperature. The mixture was stirred overnight. Ammonium chloride (5.6 g, 105 mmol) was added to the reaction solution and the solution was stirred for 2 h at 35-40° C. The solution was concentrated under vacuum to dryness and recrystallized with acetone to obtain the product, 2-c, (6.5 g, 34% for two steps). $^1$H NMR (300 MHz, CDCl$_3$): δ4.35 (s, 2H), 4.70 (s, 2H), 7.40-7.42 (m, 5H). LC-MS: (M+H)$^+$ 165.

Step C: Ethyl 2-(benzyloxymethyl)-4-hydroxypyrimidine-5-carboxylate (2-d)

Sodium (4.6 g, 200 mmol) was added to EtOH (500 mL) and the mixture was stirred until a clear solution was obtained. Then, step B product, 2-c, (20.1 g, 100 mmol) and diethyl 2-(ethoxymethylene)malonate (21.6 g, 100 mmol) were added to the clear mixture, respectively. The reaction mixture was refluxed overnight and then concentrated under vacuum, washed with EA. The wet cake was then dried to afford compound 2-d (40.0 g, crude). LC-MS: (M+H)$^+$ 289. The crude was directly used to next step without further purification.

Step D: 2-(benzyloxymethyl)-4-hydroxypyrimidine-5-carboxylic acid (2-e)

A mixture of step C product (2-d) (10.0 g, crude) in a 3% KOH solution (200 mL) was stirred at 70° C. for 1 h, then cooled to room temperature. The material then washed with DCM (200 mL×2). The aqueous phase was acidified with 5% HCl to pH 1~2, filtrated and then dried to afford product as a white solid (2-e) (6.2 g, 95% for 2 steps). $^1$H NMR (300 MHz, CD$_3$OD): δ4.56 (s, 2H), 4.72 (s, 2H), 7.33-7.40 (m, 5H), 8.61 (s, 1H), LC-MS: (M+H)$^+$ 261.

Step E: N-benzhydryl-2-(benzyloxymethyl)-4-hydroxypyrimidine-5-carboxamide (2-f)

A mixture of step D product (2-e) (20.0 g, 76.9 mmol), diphenylmethanamine (15.5 g, 84.6 mmol), HATU (43.8 g, 115.0 mmol), and TEA (23.3 g, 230 mmol) in DMF (100 mL) were combined and stirred at the ambient temperature overnight. Ice-water (40 mL) was added to the reaction mixture and extracted with DCM (30 mL×2). The organic phase was concentrated to give a residue, which was purified by silica gel chromatography (eluented with PE/EA=3:1~1:1) to a afford the product, 2-f, (31.0 g, 96%). $^1$H NMR (300 MHz, CD$_3$OD): δ4.29 (s, 2H), 4.52 (s, 2H), 6.22 (s, 1H), 7.21-7.23 (m, 15H), 8.60 (s, 1H). LC-MS: (M+H)$^+$ 426.

Step F: N-benzhydryl-4-hydroxy-2-(hydroxymethyl)pyrimidine-5-carboxamide (2-g)

A mixture of step E product, 2-f, (3.0 g, 7 mmol), ammonium formate (0.9 g, 14 mmol) and Pd/C (0.6 g) in MeOH (70 mL) was refluxed overnight. The reaction solution was filtered. The filtrate was evaporated under vacuum to obtain a residue, which was purified by silica gel chromatography by eluting with PE:EA=1:2 and DCM:MeOH=10:1 to afford the product, 2-g, (0.51 g, 21%). $^1$H NMR (300 MHz, CDCl$_3$): δ4.47 (s, 2H), 6.30-6.32 (d, Hz, 1H), 7.23-7.25 (m, 11H), 8.72 (s, 1H), 9.98-10.00 (s, 1H).

Step G: N-benzhydryl-2-formyl-4-hydroxypyrimidine-5-carboxamide (2-h)

A mixture of step F product, 2-g, (1.1 g, 3.2 mmol) and Dess-Martain reagent (1.5 g, 3.6 mmol) in DCM (50 mL) was stirred at the ambient temperature overnight. The reaction solution was washed with water and evaporated under vacuum to afford a residue (0.7 g) containing 2-h, which was directly used for next step without further purification.

Step H: 5-(benzhydrylcarbamoyl)-4-hydroxypyrimidine-2-carboxylic acid (2-i)

To a solution of step G product (2-h, 0.7 g) in t-BuOH (35 mL) was added NaH$_2$PO$_4$.12H$_2$O (0.6 g, 1.7 mmol) followed by H₂O (6 mL) and NaClO₂ (0.95 g, 10.5 mmol). After being allowed to stir at the ambient temperature overnight, the reaction mixture was evaporated under vacuum to remove t-BuOH, diluted with H₂O, treated with aq. HCl to pH 2 and the solid was filtered and the cake was washed with water and dried under vacuum to afford compound 2-i as a crude (0.35 g), which was directly used for next step without further purification.

General Procedure of Coupling Reaction:

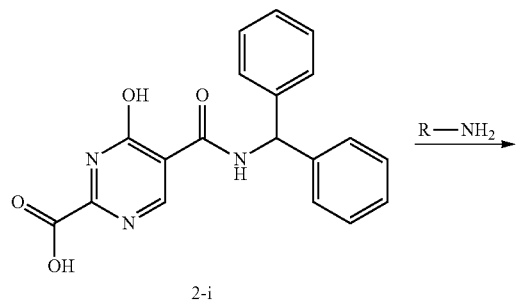

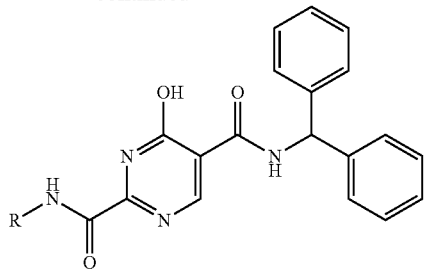

2-1~2-10

The mixture of compound 2-i (0.35 g, 1.0 mmol), a R—NH₂ (either as free base amine or HCl salt) (1.1 mmol), TBTU (400 mg) and DIPEA (300 mg) in DMSO (20 mL) was stirred at ambient temperature overnight. Then the reaction mixture was quenched with ice water (40 mL), and extracted with DCM (30 mL×2). The organic phase was concentrated to give a residue, which was purified by chromatography column (eluted with DCM/MeOH) or prep-HPLC (CH₃CN: H₂O as eluent) to afford the corresponding compounds 2-1 through 2-10 shown in Table 1.

TABLE 1

Compounds made via coupling of compound 2-i and R—NH₂.

| Comp No. | R | Compound Structure | Comp. Name | $^1$H NMR |
|---|---|---|---|---|
| 2-1 | (ethyl ester propanoyl group) | (structure) | Ethyl N-({5-[(diphenyl-methyl)carbamoyl]-4-hydroxy-pyrimidin-2-yl}carbonyl)-β-alaninate | $^1$H NMR (300 MHz, DMSO-d$_6$): δ 1.15-1.19 (t, J = 6.0 Hz, 3H), 2.60 (s, 2H), 3.49 (s, 2H), 4.01-4.08 (q, J = 3.0 Hz, 2H), 6.24-6.27 (d, J = 9.0, 1H), 7.25-7.34 (m, 10H), 8.44 (br s, 1H), 9.23-9.27 (m, 1H), 10.47 (br s, 1H) 13.57 (br s, 1H) LC-MS: (M + H)⁺ 449 |
| 2-2 | (ethyl ester group) | (structure) | Ethyl N-({5-[(diphenyl-methyl)carbamoyl]-4-hydroxy-pyrimidin-2-yl}carbonyl) glycinate | $^1$H NMR (300 MHz, DMSO-d$_6$): δ 1.19-1.23 (t, J = 6.0 Hz, 3H), 4.01-4.05 (q, J = 6.0 Hz, 2H), 6.26-6.29 (m, 1H), 7.34-7.39 (m, 10H), 9.54-9.57 (m, 1H) LC-MS: (M + Na)⁺ 457 |
| 2-3 | (methyl ester group) | (structure) | Methyl N-({5-[(diphenyl-methyl)carbamoyl]-4-hydroxy-pyrimidin-2-yl}carbonyl) glycinate | $^1$H NMR (300 MHz, CDCl₃): δ 3.83 (s, 3H), 4.23-4.25 (d, J = 3.0 Hz, 2H), 6.42-6.45 (m, 1H), 7.25-7.32 (m, 10H), 8.16-8.19 (m, 1H), 8.99 (s, 1H), 9.82-9.84 (m, 1H), 10.49 (br s, 1H) LC-MS: (M + Na)⁺ 443 |

TABLE 1-continued

Compounds made via coupling of compound 2-i and R—NH$_2$.

| Comp No. | R | Compound Structure | Comp. Name | $^1$H NMR |
|---|---|---|---|---|
| 2-4 | | 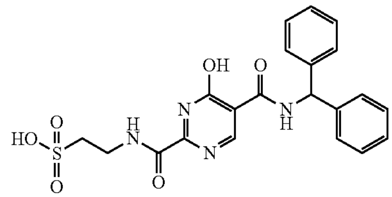 [SMILES: O=C(NCCS(=O)(=O)O)c1ncc(C(=O)NC(c2ccccc2)c2ccccc2)c(O)n1] | 2-[({5-[(diphenylmethyl)carbamoyl]-4-hydroxypyrimidin-2-yl}carbonyl)amino]ethanesulfonic acid | $^1$H NMR (300 MHz, DMSO-d$_6$): δ 2.65-2.69 (t, J = 6.0 Hz, 6H), 3.52-3.56 (t, J = 6.0 Hz, 6H), 6.25-6.27 (d, J = 6.0 Hz, 1H), 7.26-7.36 (m, 10H), 8.48 (s, 1H), 9.24-9.27 (m, 1H), 10.38-10.40 (m, 1H). LC-MS: (M − H)$^−$ 455 |
| 2-5 | | 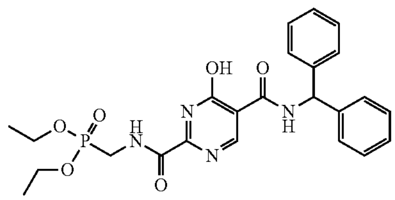 [SMILES: CCOP(=O)(CNC(=O)c1ncc(C(=O)NC(c2ccccc2)c2ccccc2)c(O)n1)OCC] | Diethyl {[({5-[(diphenylmethyl)carbamoyl]-4-hydroxypyrimidin-2-yl}carbonyl)amino]methyl}phosphonate | $^1$H NMR (300 MHz, DMSO-d$_6$): δ 1.20-1.25 (t, J = 6.0 Hz, 6H), 3.70-3.78 (m, 2H), 4.00-4.07 (q, J = 6.0 Hz, 4H), 6.25-6.28 (m, 1H), 7.25-7.34 (m, 10H), 8.55 (s, 1H), 9.16-9.18 (m, 1H), 10.89-10.91 (m, 1H). LC-MS: (M + H)$^+$ 499 |
| 2-6 | | 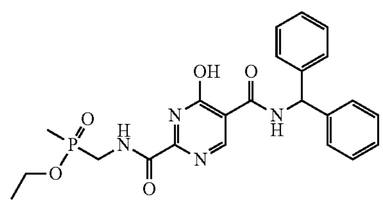 [SMILES: CCOP(C)(=O)CNC(=O)c1ncc(C(=O)NC(c2ccccc2)c2ccccc2)c(O)n1] | Ethyl {[({5-[(diphenylmethyl)carbamoyl]-4-hydroxypyrimidin-2-yl}carbonyl)amino]methyl}methyl-phosphinate | $^1$H NMR (300 MHz, DMSO-d$_6$): δ 1.20-1.25 (t, J = 6.0 Hz, 3H), 1.42-1.47 (t, J = 15.0 Hz, 3H), 3.63-3.66 (m, 2H), 3.98-4.03 (q, J = 6.0 Hz, 2H), 6.25-6.28 (m, 1H), 7.25-7.34 (m, 10H), 8.55 (s, 1H), 9.14-9.18 (m, 1H), 11.10 (br s, 1H). LC-MS: (M + Na)$^+$ 491 |
| 2-7 | | 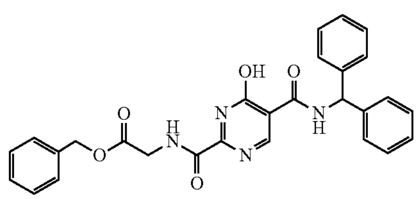 [SMILES: O=C(CNC(=O)c1ncc(C(=O)NC(c2ccccc2)c2ccccc2)c(O)n1)OCc1ccccc1] | Benzyl N-({5-[(diphenyl-methyl)carbamoyl]-4-hydroxy-pyrimidin-2-yl}carbonyl) glycinate | $^1$H NMR (300 MHz, DMSO-d$_6$): δ 4.09-4.11 (d, J = 6.0 Hz, 2H), 5.17 (s, 2H), 6.27-6.29 (m, 1H), 7.30-7.36 (m, 15H), 8.48 (br s, 1H), 9.54-9.57 (m, 1H), 10.49 (br s, 1H), 13.63 (br s, 1H) LC-MS: (M − H)$^−$ 495 |
| 2-8 | | 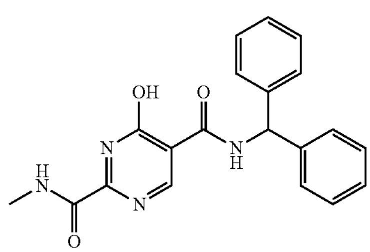 [SMILES: CNC(=O)c1ncc(C(=O)NC(c2ccccc2)c2ccccc2)c(O)n1] | N$^5$-(diphenylmethyl)-4-hydroxy-N$^2$-methylpyrimidine-2,5-dicarboxamide | $^1$H NMR (300 MHz, DMSO-d$_6$): δ 2.80 (s, 3H), 6.24-6.27 (d, J = 6.0 Hz, 1H), 7.25-7.37 (m, 10H), 8.45 (br s, 1H), 9.18 (s, 1H), 10.38 (br s, 1H) LC-MS: (M + Na)$^+$ 385 |
| 2-9 | | 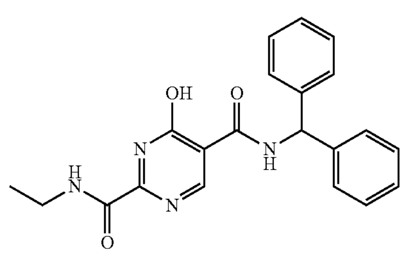 [SMILES: CCNC(=O)c1ncc(C(=O)NC(c2ccccc2)c2ccccc2)c(O)n1] | N$^5$-(diphenylmethyl)-4-hydroxy-N$^2$-ethylpyrimidine-2,5-dicarboxamide | $^1$H NMR (300 MHz, D$_2$O + DMSO-d$_6$): δ 1.07-1.12 (d, J = 6.0 Hz, 3H), 3.26-3.28 (m, 2H), 6.23 (s, 1H), 7.25-7.35 (m, 10H), 8.50 (s, 1H) LC-MS: (M + Na)$^+$ 399 |

TABLE 1-continued

Compounds made via coupling of compound 2-i and R—NH$_2$.

| Comp No. | R | Compound Structure | Comp. Name | $^1$H NMR |
|---|---|---|---|---|
| 2-10 | (isoxazol-4-yl)methyl | 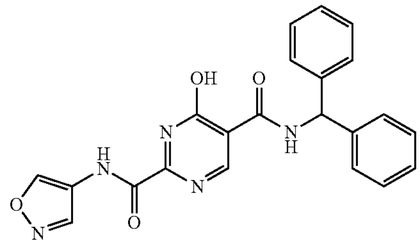 [SMILES: O=C(Nc1cnoc1)c1ncc(C(=O)NC(c2ccccc2)c2ccccc2)c(O)n1] | N$^5$-(diphenylmethyl)-4-hydroxy-N$^2$-(4-isoxazolyl)pyrimidine-2,5-dicarboxamide | $^1$H NMR (300 MHz, DMSO-d$_6$) δ 6.27-6.30 (d, J = 9.0 Hz, 1H), 7.27-7.36 (m, 11H), 8.85 (s, 1H), 9.34 (s, 1H), 11.65 (s, 1H). LC-MS: (M + Na)$^+$ 438 |

Example 2-11

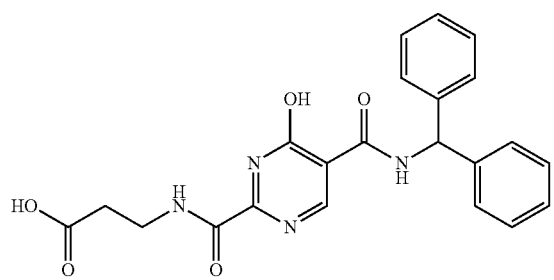

3-(5-(benzhydrylcarbamoyl)-4-hydroxypyrimidine-2-carboxamido)propanoic acid (2-11)

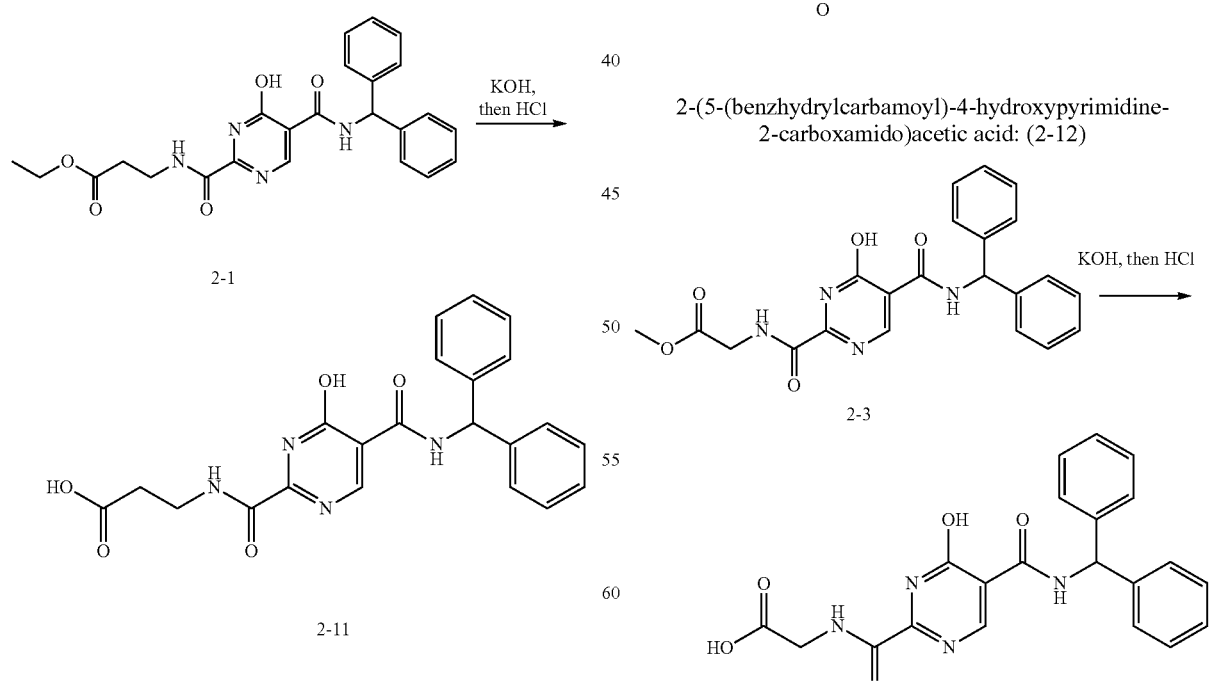

Compound 2-1 (210 mg, 0.47 mmol) was added to a 10% KOH solution (30 mL). The resulting mixture was stirred at 50° C. for 30 min and then cooled to room temperature. The cooled reaction solution was then washed with DCM (30 mL×2). The resulting aqueous phase was acidified with 5% HCl to approximately of about pH=12. The solids were collected via filtration, and dried to afford compound 2-11 as a white solid (174 mg, 88%): $^1$H NMR (300 MHz, DMSO-d$_6$): δ 3.45-3.52 (m, 2H), 6.26-6.28 (m, 1H), 7.33-7.36 (m, 10H), 8.49 (s, 1H), 9.17-9.21 (m, 1H), 10.42 (s, 1H). LC-MS: (M+H)$^+$ 421.

Example 2-12

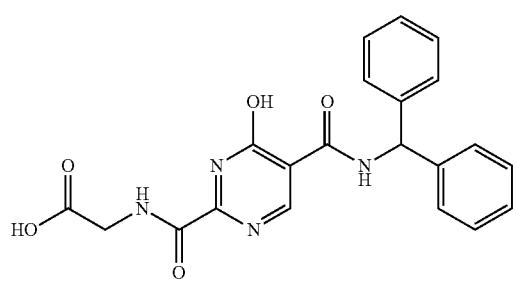

2-(5-(benzhydrylcarbamoyl)-4-hydroxypyrimidine-2-carboxamido)acetic acid: (2-12)

Compound 2-12 was prepared in a similar manner as compound 2-11 from compound 2-3. For compound 2-12: ¹H NMR (300 MHz, DMSO-d₆): δ 4.11 (s, 2H), 6.29-6.32 (d, J=8.1 Hz, 1H), 7.24-7.32 (m, 10H), 8.74 (s, 1H), 10.49 (br s, 1H) LC-MS: (M+H)⁺ 407.

Examples 2-13 and 2-14

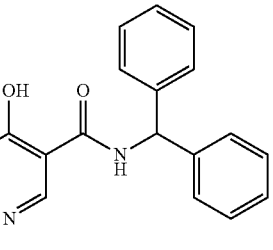

2-13

{[({5-[(diphenylmethyl)carbamoyl]-4-hydroxypyrimidin-2-yl}carbonyl)amino]methyl}phosphonicacid (2-13)

To a solution of 2-5 (0.2 mmol) in anhydrous dichloromethane (50 mL) was added TMSBr (1.5 mL) dropwise at 0° C. The mixture was then warmed to room temperature and stirred overnight. The pH of mixture was adjusted to about 5 or 6. The mixture was then concentrated. The residue was purified by pre-HPLC to afford the titled compound, 2-13. For compound 2-13: ¹H NMR (300 MHz, DMSO-d₆): δ 3.51-3.57 (m, 2H), 6.24-6.27 (m, 1H), 7.25-7.38 (m, 10H), 8.86-8.89 (m, 1H). LC-MS: (M+Na)⁺ 465; (M−H)⁻ 441.

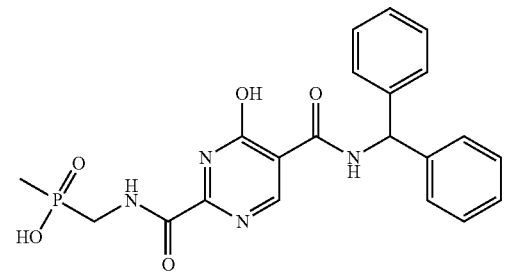

2-14

{[({5-[(diphenylmethyl)carbamoyl]-4-hydroxypyrimidin-2-yl}carbonyl)amino]methyl}methylphosphinicacid (2-14)

Compound 2-14 was prepared from compound 2-6 in a similar manner as the synthesis of compound 2-13. For compound 2-14: ¹H NMR (300 MHz, DMSO-d₆): δ 1.33-1.37 (d, J=14.1 Hz, 3H), 3.53-3.58 (m, 2H), 6.25-6.28 (m, 1H), 7.25-7.37 (m, 10H), 9.27-9.32 (m, 1H). LC-MS: (M+H)⁺ 463; (M−H)⁻ 439.

Example 2-15

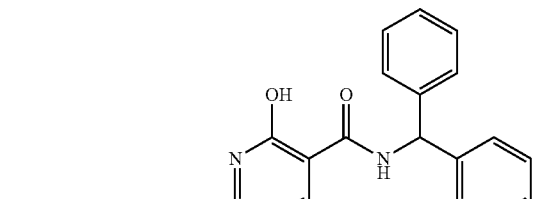

2-15

Step A: (E)-N-(diphenylmethyl)-4-hydroxy-2-[(E)-(hydroxyimino)methyl]pyrimidine-5-carboxamide (2-15-1)

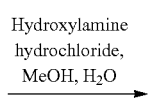

2-h

Hydroxylamine hydrochloride, MeOH, H₂O →

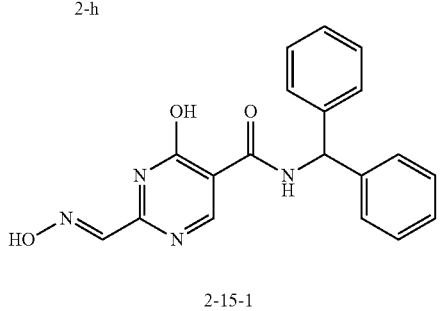

2-15-1

A mixture of compound 2-h (3.4 g, 10.2 mmol), NaOAc (1.68 g, 20.4 mmool) and hydroxyamine hydrochloride (1.06 g, 15.6 mmol) in H₂O (75 mL) was stirred at 100° C. for 3 h. The resulting precipitate was isolated by filtration to afford the product, 2-15-1 as a solid (2.0 g). ¹H NMR (300 MHz, DMSO-d₆) δ 12.49 (s, 1H), 7.91 (s, 1H), 7.35-7.33 (m, 11H), 6.26 (d, J=8.1 Hz, 1H). LC-MS: (M+H)⁺ 349.

Step B: Ethyl 3-{[5-(diphenylmethyl)carbamoyl]-4-hydroxypyrimidin-2-yl}isoxazole-5-carboxylic acid (2-15)

To a solution of step A product (2-15-1, 2.0 g, 5.7 mmol) in DMF (30 mL), was added NCS (0.99 g, 7.4 mmol) at room temperature. The reaction mixture was heated at 60° C. for 1 h. The reaction mixture was then cooled to 0° C. and ethyl propiolate (1.58 g, 16 mmol) was added. Then Et₃N (0.7 g, 6.8 mmol) in DMF (10 mL) was added dropwise over 30 min.

The reaction mixture was slowly allowed to warm to room temperature and stirred overnight. The mixture was diluted with water (50 mL) and extracted with EA (100 mL). The organic layer was washed with brine (50 mL), dried over $Na_2SO_4$, and concentrated under vacuum. The collected residue was purified by column chromatography with the eluent (PE:EA=3:1 to 1:1) to afford compound 2-15 (500 mg, 20%). $^1$H NMR (300 MHz, DMSO-$d_6$) δ 8.68 (s, 1H), 7.77 (s, 1H), 7.44-7.25 (m, 11H), 6.29 (d, J=8.1 Hz, 1H), 4.43 (t, J=7.2 Hz, 2H), 1.35 (t, J=7.2 Hz, 3H). LC-MS: (M+H)$^+$ 445.1.

Example 2-16

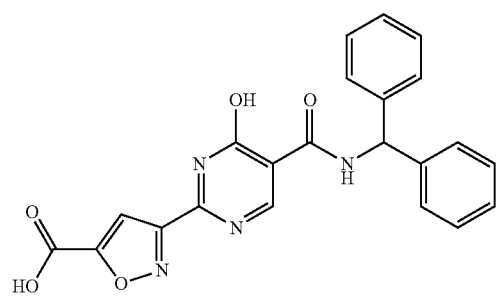

3-{[5-(diphenylmethyl)carbamoyl]-4-hydroxypyrimidin-2-yl}isoxazole-5-carboxylic acid (2-16)

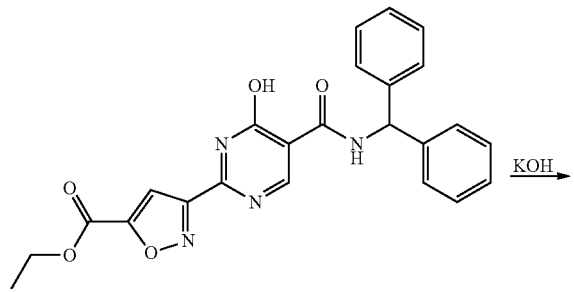

KOH (214 mg, 3.8 mmol) was added to a solution of compound 2-15 (170 mg, 0.38 mmol) in $H_2O$ (20 mL) and stirred at 50° C. for 30 min. The reaction mixture was extracted with EA (20 mL). The aqueous layer was adjusted to pH 2 by addition of HCl. The solids were filtered to afford compound 2-16 as a white solid (140 mg, 88%). $^1$H NMR (300 MHz, DMSO-$d_6$). δ 10.53 (d, J=7.5 Hz, 1H), 8.62 (s, 1H), 7.36-7.24 (m, 11H), 6.25 (d, J=4.2 Hz, 1H,). LC-MS: (M+Na)$^+$ 439.

Example 2-17

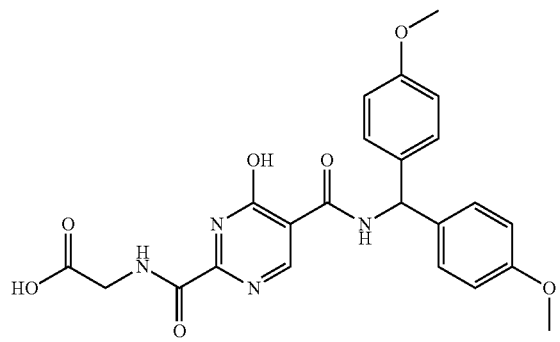

Synthesis of Compound 2-17

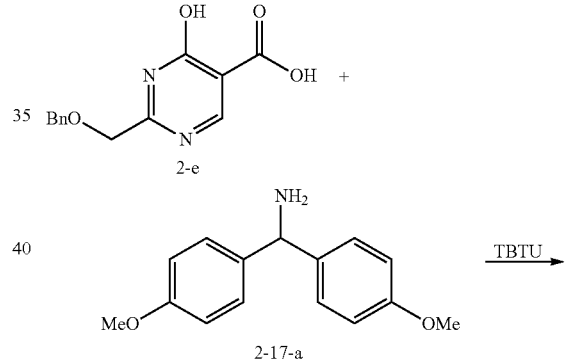

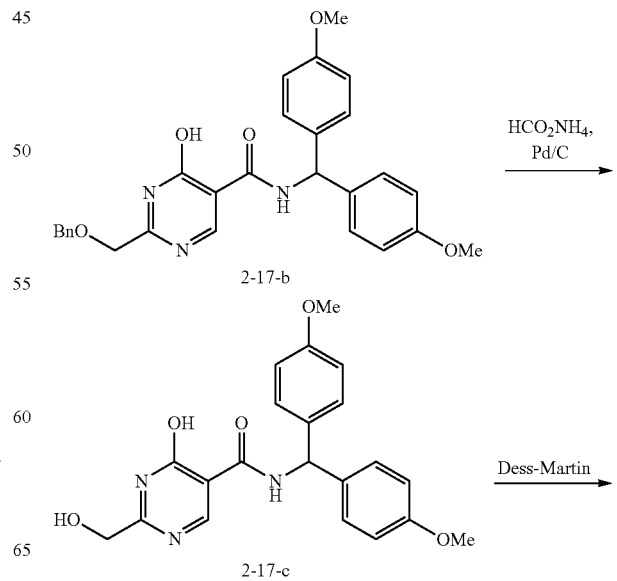

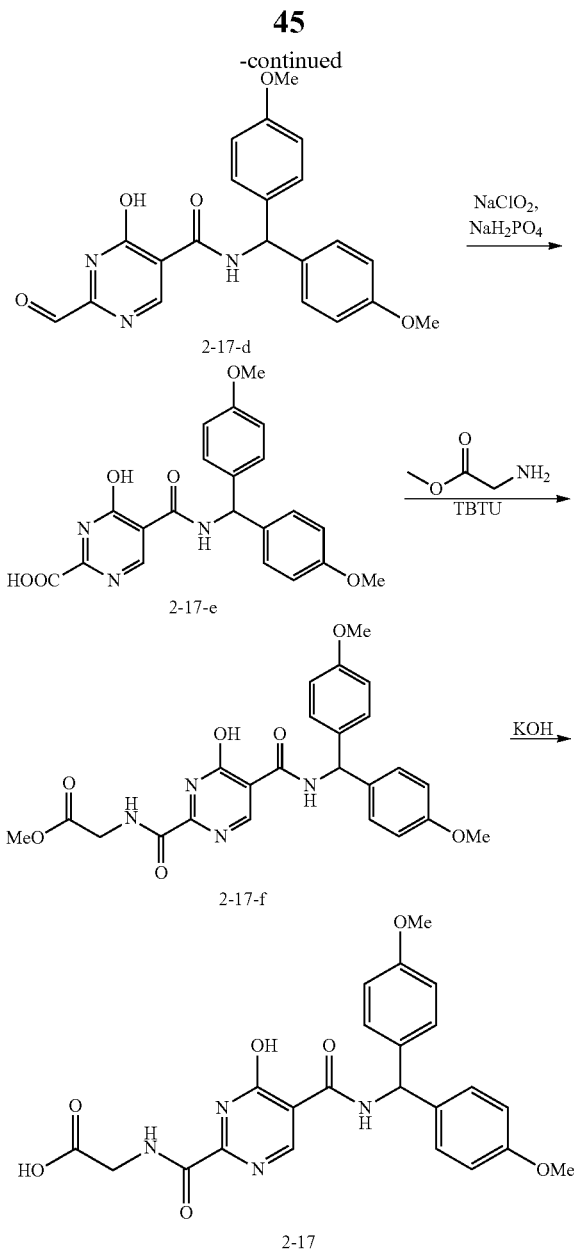

Step B: N-(bis(4-methoxyphenyl)methyl)-4-hydroxy-2-(hydroxymethyl)pyrimidine-5-carboxamide (2-17-c)

A mixture of step A product, compound 2-17-b, (5.7 g, 11.7 mmol), ammonium formate (1.5 g, 23.5 mmol) and Pd/C (1.0 g) in MeOH (120 mL) was refluxed. The reaction was monitored by TLC. The reaction solution was filtered. The filtration was evaporated under vacuum to obtain a residue, which was purified by column chromatography eluting with DCM:MeOH=40:1 to afford the title compound (2.0 g, 43%) as white solid. $^1$H NMR (300 MHz, DMSO-$d_6$): δ 3.72 (s, 6H), 4.43-4.45 (d, J=6 Hz, 2H), 6.13-6.15 (d, J=7.5 Hz, 1H), 6.87-6.90 (m, 4H), 7.16-7.18 (m, 4H), 8.51 (s, 1H). LC-MS: (M+H)$^+$ 396.

Step C: N-(bis(4-methoxyphenyl)methyl)-2-formyl-4-hydroxypyrimidine-5-carboxamide (2-17-d)

A mixture of step B product, 2-17-c, (2.0 g, 5 mmol) and Dess-Martain reagent (2.4 g, 5.6 mmol) in DCM (60 mL) was stirred at the ambient temperature for 1 h. The reaction solution was evaporated under vacuum to give a residue, which was purified by column chromatography with the eluent DCM:MeOH=60:1 to afford the crude product, 2-17-d, (1.84 g, 84%) as a solid. LC-MS: (M+H$_3$O)$^+$ 416.

Step D: 5-(bis(4-methoxyphenyl)methylcarbamoyl)-4-hydroxypyrimidine-2-carboxylic acid (2-17-e)

To a solution of compound 2-17-d (2.4 g, 6.1 mmol) in t-BuOH (40 mL) was added NaH$_2$PO$_4$.12H$_2$O (1.75 g, 4.9 mmol) followed by H$_2$O (7 mL) and NaCl$_2$ (1.65 g, 18.3 mmol). After being allowed to stir at the ambient temperature for 2 h, the reaction mixture was filtered and the filtrate was concentrated in vacuo to give crude compound, 2-17-e, (2.5 g), which was used for next step without further purification. LC-MS: (M−H)$^-$ 408.

Step E: Methyl 2-(5-(bis(4-methoxyphenyl)methylcarbamoyl)-4-hydroxypyrimidine-2carboxamido)acetate (2-17-f)

The mixture of compound 2-17-e (2.5 g, 6.1 mmol), methyl 2-aminoacetate hydrochloride (0.92 g, 7.3 mmol), TBTU (2.4 g, 7.3 mmol), DIPEA (1.6 g, 12.2 mmol) in DMSO (15 mL) and stirred at the ambient temperature overnight. Ice-water was then added to the reaction mixture and filtered. The cake was purified by column chromatography with DCM:MeOH=100:1~50:1 to obtain the product, 2-17-f, (630 mg, 22%). LC-MS: (M+H)$^+$ 481.

Step F: 2-(5-(bis(4-methoxyphenyl)methylcarbamoyl)-4-hydroxypyrimidine-2-carboxamido)acetic acid (2-17)

Step E product, 2-17-f, (300 mg, 0.63 mmol) was added to the solution of KOH (340 mg) in H$_2$O (20 mL). The mixture was heated to 50° C. for 30 min, then cooled to room temperature, and subsequently washed with EA (30 mL×2). The aqueous phase was acidified with 5% HCl to about a pH 1~2, filtrated and dried to afford compound 2-17 as a pale brown solid. (157 mg, 54%). $^1$H NMR (300 MHz, DMSO-$d_6$): δ 3.72 (s, 6H), 3.92-3.94 (d, J=6 Hz, 2H), 6.14-6.17 (d, J=9 Hz, 1H), 6.91 (d, J=9 Hz, 4H), 7.17-7.20 (d, J=9 Hz, 4H), 8.50 (s, 1H), 9.30-9.34 (m, 1H), 10.41-10.43 (m, 1H). LC-MS: (M−H)$^-$ 465.

Step A: 2-(benzyloxymethyl)-N-(bis(4-methoxyphenyl)methyl)-4-hydroxypyrimidine-5-carboxamide (2-17-a)

TBTU (296 mg, 0.92 mmol) and DIPEA (119 mg, 0.92 mmol) were added to a stirred suspension of compound 2-e (200 mg, 0.77 mmol) in DMSO (1.5 mL). The reaction mixture was stirred at ambient temperature until the soluble material dissolved. Compound 2-17-a (206 mg, 0.85 mmol) in DMF (0.5 mL) was added to the reaction mixture via syringe. After being allowed to stir at room temperature overnight, the reaction mixture was poured into ice-water and extracted with DCM and then subsequently concentrated to give a residue. The residue was purified by column chromatography with the eluent PE:EA=100:1~1:1 to afford compound 2-17-b (151 mg, 40%). $^1$H NMR (300 MHz, CDCl$_3$): δ 3.78 (s, 6H), 4.54 (s, 2H), 4.71 (s, 2H), 6.31-6.34 (d, J=8.4 Hz, 1H), 6.83-6.86 (m, 4H), 7.20-7.23 (m, 4H), 7.35-7.38 (m, 5H), 8.89 (s, 1H). LC-MS: (M+H)$^+$ 486.

Compound 2-18

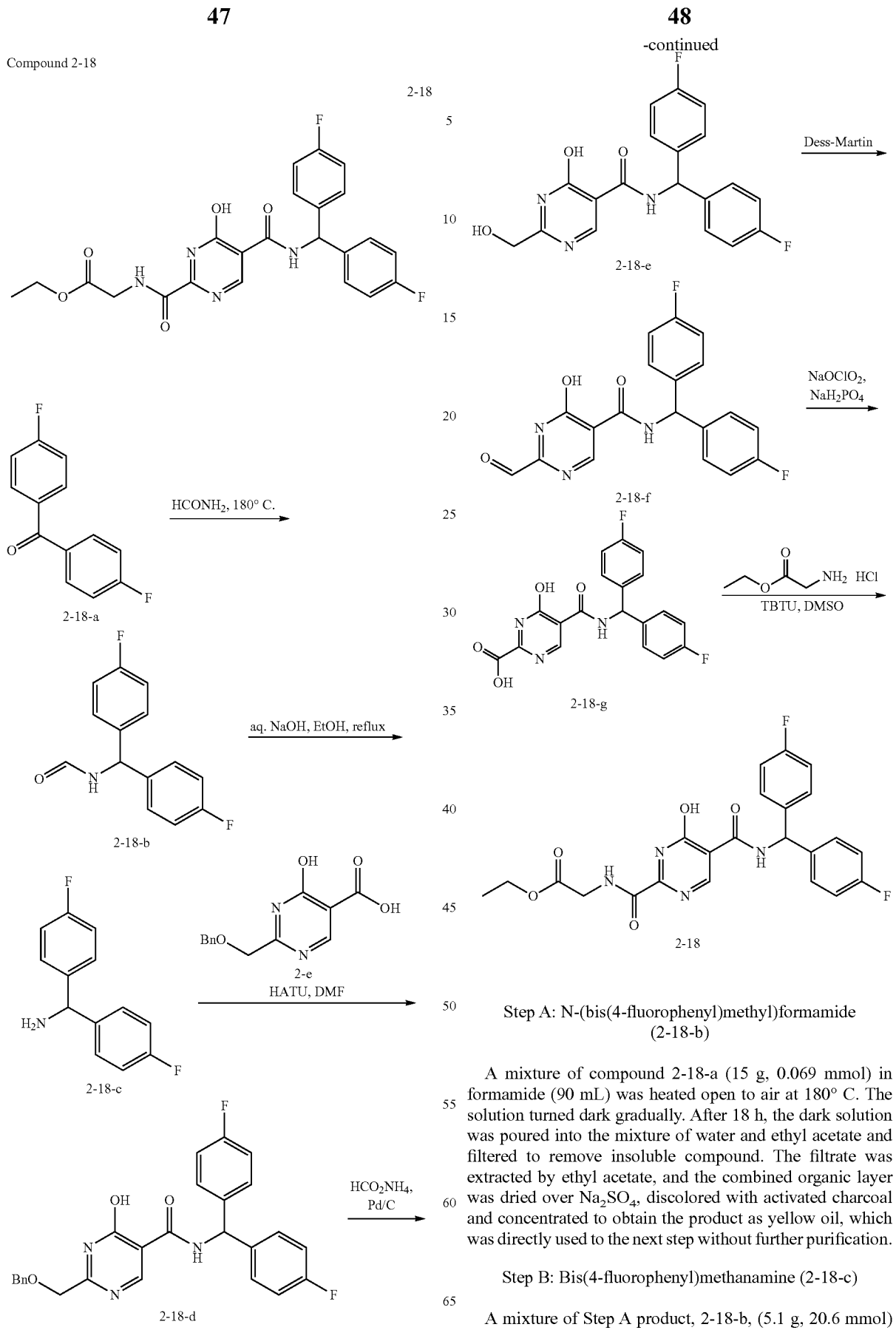

Step A: N-(bis(4-fluorophenyl)methyl)formamide (2-18-b)

A mixture of compound 2-18-a (15 g, 0.069 mmol) in formamide (90 mL) was heated open to air at 180° C. The solution turned dark gradually. After 18 h, the dark solution was poured into the mixture of water and ethyl acetate and filtered to remove insoluble compound. The filtrate was extracted by ethyl acetate, and the combined organic layer was dried over $Na_2SO_4$, discolored with activated charcoal and concentrated to obtain the product as yellow oil, which was directly used to the next step without further purification.

Step B: Bis(4-fluorophenyl)methanamine (2-18-c)

A mixture of Step A product, 2-18-b, (5.1 g, 20.6 mmol) and aq. NaOH (40%, 56 mL) in ethanol (280 mL) was refluxed overnight. The reaction mixture was concentrated to remove ethanol. The resulting solution was extracted by DCM, the combined organic layer was washed with brine, dried over $Na_2SO_4$ and concentrated to give a residue. The residue was purified by column chromatography, eluting with PE:EA=5:1 to 3:1 to obtain the product, 2-18-c, (3.32 g, 74%). $^1$H NMR (300 MHz, $CDCl_3$): δ 1.1.71-1.73 (m, 2H), 5.20 (s, 1H), 6.97-7.03 (m, 4H), 7.30-7.35 (m, 4H). LC-MS: $(M+H)^+$ 220.

Step C: 2-(benzyloxymethyl)-N-(bis(4-fluorophenyl) methyl)-4-hydroxypyrimidine-5-carboxamide (2-18-d)

HATU (8.63 g, 23 mmol) and $Et_3N$ (6.13 g, 61 mmol) were added to a stirred suspension of the product of step B, 2-18-c, (4.10 g, 16 mmol) in $CH_3CN$ (90 mL). The reaction mixture was stirred at ambient temperature until all solids dissolved. To this stirred solution was added compound 2-e (3.32 g, 15 mmol) in $CH_3CN$ (10 mL) via syringe. The solution was stirred at room temperature overnight, and then was poured into ice-water (300 mL), extracted with DCM, and then concentrated to give a residue. The residue was purified by column chromatography with the eluent PE:EA=3:1~2:1 to afford the product, 2-18-d, (5.3 g, 79%). $^1$H NMR (300 MHz, $CDCl_3$): δ 4.54 (s, 2H), 4.69 (s, 2H), 6.36-6.39 (d, J=9 Hz, 1H), 6.98-7.04 (m, 4H), 7.24-7.26 (m, 4H), 7.31-7.40 (m, 5H), 8.89 (s, 1H), 9.73 (m, 1H). LC-MS: $(M+H)^+$ 448.

Step D: N-(bis(4-fluorophenyl)methyl)-4-hydroxy-2-(hydroxymethyl)pyrimidine-5-carboxamide (2-18-e)

A mixture of step C product, 2-18-d, (5.3 g, 11.8 mmol), ammonium formate (1.5 g, 23.7 mmol) and Pd/C (1.0 g) in MeOH (400 mL) was refluxed. The reaction was monitored by TLC. The reaction solution was filtered. The filtration was evaporated under vacuum to obtain a residue, which was purified by column chromatography eluting with DCM:MeOH=50:1~30:1 to afford the product, 2-18-e, (2.0 g, 45%) as white solid. $^1$H NMR (300 MHz, $CD_3OD$): δ 4.58 (s, 2H), 6.30-6.31 (d, J=3.0 Hz, 1H), 7.05-7.11 (m, 4H), 7.29-7.34 (m, 4H), 8.64 (s, 1H) LC-MS: $(M+H)^+$ 372.3.

Step E: N-(bis(4-fluorophenyl)methyl)-2-formyl-4-hydroxypyrimidine-5-carboxamide (2-18-f)

A mixture of step D product, 2-18-e, (2.0 g, 5.4 mmol) and Dess-Martain reagent (2.5 g, 5.9 mmol) in DCM (100 mL) was stirred at the ambient temperature for 4 h. The reaction solution was evaporated under vacuum to give a residue. The residue was purified by column chromatography with the eluent DCM:MeOH=70:1 to afford the crude product, 2-18-f, (2.1 g). LC-MS: $(M+H_3O)^+$ 387.

Step F: 5-(bis(4-fluorophenyl)methylcarbamoyl)-4-hydroxypyrimidine-2-carboxylic acid (2-18-2)

To a solution of step E product, 2-18-f, (2.1 g, 5.7 mmol) in t-BuOH (35 mL) was added $NaH_2PO_4.12H_2O$ (1.6 g, 4.6 mmol) followed by $H_2O$ (5 mL) and $NaClO_2$ (2.4 g, 26 mmol). After being allowed to stir at the ambient temperature for 4 h, the reaction mixture was filtered and ethyl acetate was added. The filtrate was concentrated to give a crude product, which was directly used to the next step without further purification. LC-MS: $(M-H)^-$ 384.

Step G: Ethyl 2-(5-(bis(4-fluorophenyl)methylcarbamoyl)-4-hydroxypyrimidine-2-carboxamido)acetate (2-18)

The mixture of compound 2-18-g (1 g, 2.6 mmol), ethyl 2-aminoacetate hydrochloride (435 mg, 3.1 mmol), TBTU (1.0 g, 3.1 mmol), and DIPEA (1.2 g, 9.3 mmol) in DMSO (20 mL) was stirred at the ambient temperature overnight. The reaction mixture was then added ice-water (40 mL) and extracted with DCM (30 mL×2). The organic phase was concentrated to give a residue, which was purified by pre-HPLC ($CH_3CN:H_2O$ as eluent) to obtain 2-18 (70 mg, 6%). $^1$H NMR (300 MHz, DMSO-$d_6$): δ 1.18-1.23 (t, 3H), 4.0-4.02 (d, J=6 Hz, 2H), 4.09-4.16 (q, 2H), 6.29-6.31 (d, J=6 Hz, 1H), 7.16-7.22 (m, 4H), 7.33-7.38 (m, 4H), 9.52 (m, 1H). LC-MS: $(M+Na)^+$ 493.

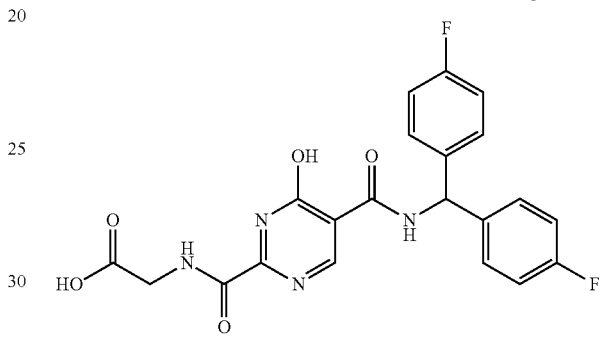

Compound 2-19

2-(5-(bis(4-fluorophenyl)methylcarbamoyl)-4-hydroxypyrimidine-2-carboxamido) acetic acid (2-19)

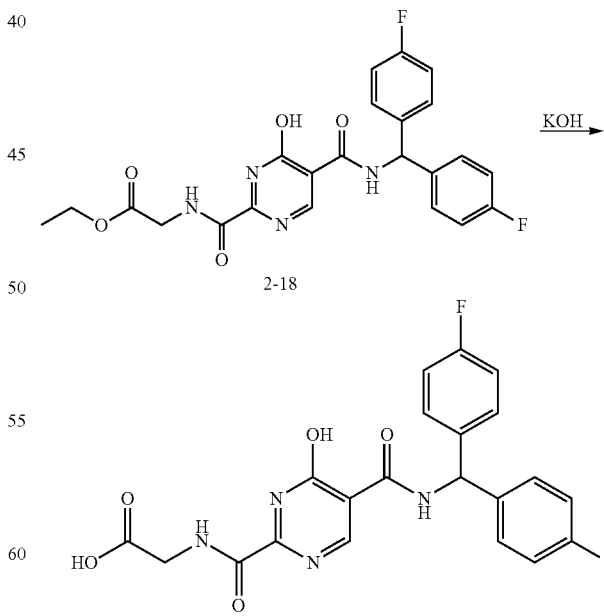

To a 10% KOH solution (30 mL) was added compound 2-18 (53 mg, 0.11 mmol), and the mixture was stirred at 50° C. for 30 min, then cooled to room temperature. The cooled mixture was washed with DCM (30 mL×2). The aqueous phase was acidified with 5% HCl to about a pH 2~3, filtrated and dried to afford compound 2-19 as a white solid (42 mg, 85%). $^1$H NMR (300 MHz, DMSO-$d_6$): δ 3.92-3.95 (d, J=9.0 Hz, 2H), 6.28-6.31 (d, J=9.0 Hz, 2H), 7.18-7.34 (m, 8H), 8.47 (s, 1H), 9.36-9.39 (m, 1H), 10.33 (br s, 1H). LC-MS: (M+Na)$^+$ 465.

Compound 2-20

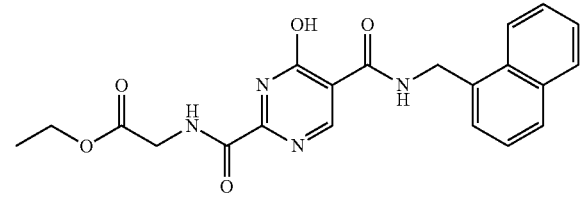

2-20

Synthesis of 2-20

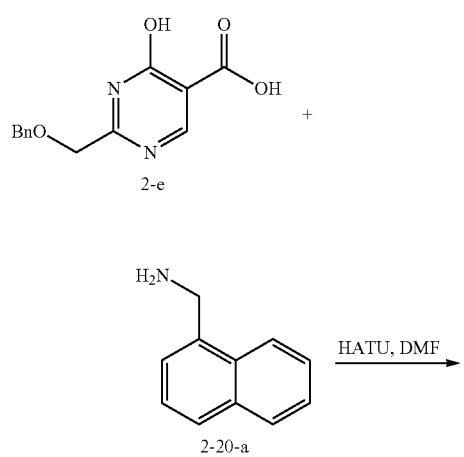

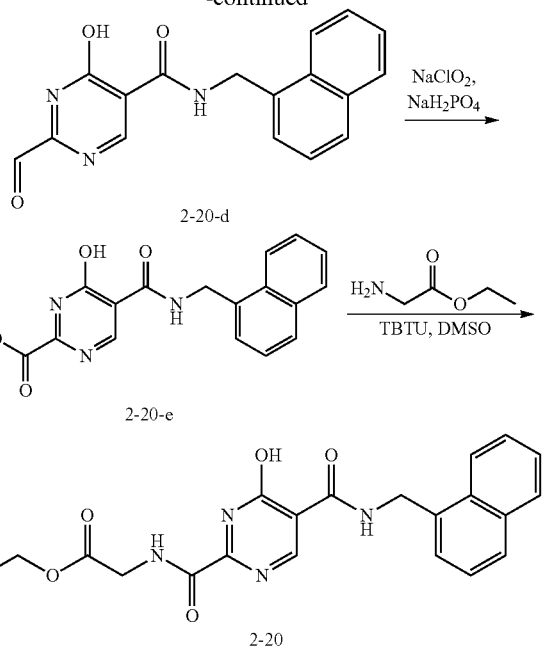

Step A: 2-(benzyloxymethyl)-4-hydroxy-N-(naphthalen-1-ylmethyl)pyrimidine-5-Carboxamide (2-20-b)

To a stirred suspension of compound 2-e (7.5 g, 28.9 mmol) in DMF (50 mL) was added HATU (12 g, 31.8 mmol) and DIPEA (4.1 g, 31.8 mmol). The reaction mixture was stirred at ambient temperature until all material was dissolved. Compound 2-20-a (5 g, 31.8 mmol) in DMF (20 mL) was added to the stirred solution via syringe. The solution was stirred at room temperature overnight. The reaction mixture was poured into ice-water (300 mL) and extracted with DCM and subsequently concentrated to give a residue. The dried residue was purified by column chromatography with the eluent PE:EA=3:1~2:1 to afford the product, 2-20-b, (1.8 g, 16%). $^1$H NMR (300 MHz, CDCl$_3$): δ 4.51 (s, 2H), 4.65 (s, 2H), 5.08-5.10 (d, J=6 Hz, 2H), 7.31-7.52 (m, 10H), 7.78-7.88 (m, 3H), 8.96 (s, 1H). LC-MS: (M+H)$^+$ 400.

Step B: 4-hydroxy-2-(hydroxymethyl)-N-(naphthalen-1-ylmethyl)pyrimidine-5-carboxamide (2-20-c)

A mixture of the step A product, 2-20-b, (7.4 g, 18.5 mmol), ammonium formate (4.7 g, 74.1 mmol) and Pd/C (3.0 g) in MeOH (300 mL) was refluxed. The reaction was monitored by TLC. The reaction solution was filtered. The filtration was evaporated under vacuum to obtain a residue, which was purified by column chromatography eluting with DCM:MeOH=80:1~15:1 to afford the product, 2-20-c, (1.47 g) as white solid. LC-MS: (M+H)$^+$ 310.

Step C: 2-formyl-4-hydroxy-N-(naphthalen-1-ylmethyl)pyrimidine-5-carboxamide (2-20-d)

A mixture of step B product, 2-20-c, (2.22 g, 7.2 mmol) and Dess-Martain reagent (3.35 g, 7.9 mmol) in DCM (80 mL) was stirred at the ambient temperature for 1 h. The reaction solution was evaporated under vacuum to give a residue, which was purified by column chromatography with the elu-

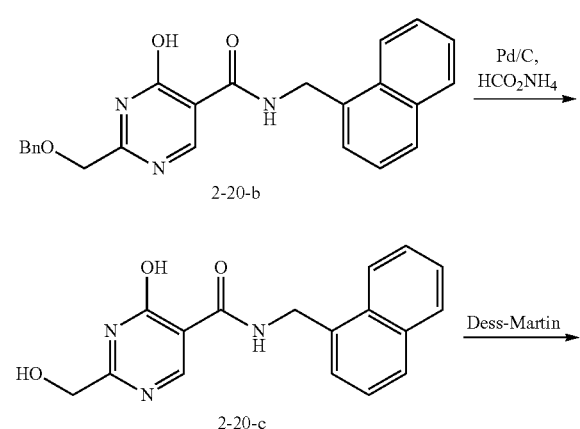

ent DCM:MeOH=60:1~30:1 to afford the crude compound, 2-20-d, (1.84 g, 84%) as a solid.

Step D: 4-hydroxy-5-(naphthalen-1-ylmethylcarbamoyl)pyrimidine-2-carboxylic acid (2-20-e)

To a solution of compound 2-20-d (1.84 g, 6 mmol) in t-BuOH (30 mL) was added $NaH_2PO_4.12H_2O$ (1.72 g, 4.8 mmol) followed by $H_2O$ (9 mL) and $NaClO_2$ (1.63 g, 18 mmol). After being allowed to stir at the ambient temperature for 4 h, the reaction mixture was filtered and collected the filtrate cake to obtain a crude product, 2-20-e, (2.4 g), which was reacted directly in the next step without further purification. LC-MS: $(M-H)^-$ 322.

Step E: Ethyl-2-(4-hydroxy-5-(naphthalen-1-ylmethylcarbamoyl)pyrimidine-2-carboxamido)acetate (2-20)

The mixture of step D product, 2-20-e, (2.5 g, 7.7 mmol), ethyl 2-aminoacetate hydrochloride (1.29 g, 9.3 mmol), TBTU (2.98 g, 9.3 mmol), DIPEA (2.0 g, 15.5 mmol) in DMSO (20 mL) and stirred at the ambient temperature overnight. Then the reaction mixture was added ice-water (40 mL), extracted with DCM (30 mL×2). The organic phase was concentrated to give a residue, which was purified by column chromatography with DCM:MeOH=150:1 to obtain 2-20 (330 mg, 11%). $^1$H NMR (300 MHz, DMSO-$d_6$): δ 1.18-1.22 (t, J=6 Hz, 3H), 4.0-4.02 (d, J=6 Hz, 2H), 4.11-4.14 (q, J=6.0 Hz, 2H), 5.0-5.02 (d, J=6.0 Hz, 1H), 7.48-7.57 (m, 4H), 7.87 (m, 3H), 8.55 (br s, 1H), 9.48 (m, 1H), 9.87 (br s, 1H), 13.54 (br s, 1H). LC-MS: $(M+H)^+$ 409.

2-(4-hydroxy-5-(naphthalen-1-ylmethylcarbamoyl)pyrimidine-2-carboxamido)acetic acid (2-21)

Compound 2-20 (300 mg, 0.67 mmol) was added to a 10% KOH solution (30 mL) and stirred at 50° C. for 30 min, then cooled to room temperature, washed with DCM (30 mL×2). The aqueous phase was acidified with 5% HCl to pH 23 and filtrated and dried to afford compound 2-21 as a white solid (200 mg, 79%). $^1$H NMR (300 MHz, DMSO-$d_6$): δ 3.92-3.94 (d, J=6.0 Hz, 2H), 5.0-5.01 (d, J=3.0 Hz, 2H), 7.48-7.54 (m, 4H), 7.55-7.57 (m, 3H), 8.44 (br s, 1H), 9.40 (m, 1H), 9.93 (br s, 1H), 12.80 (br s, 1H), 13.56 (br s, 1H). LC-MS: $(M-H)^-$ 379.

Example 2-22

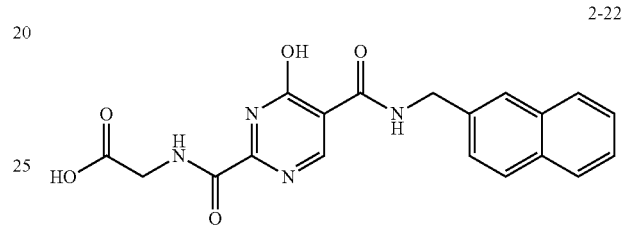

Synthesis of 2-22

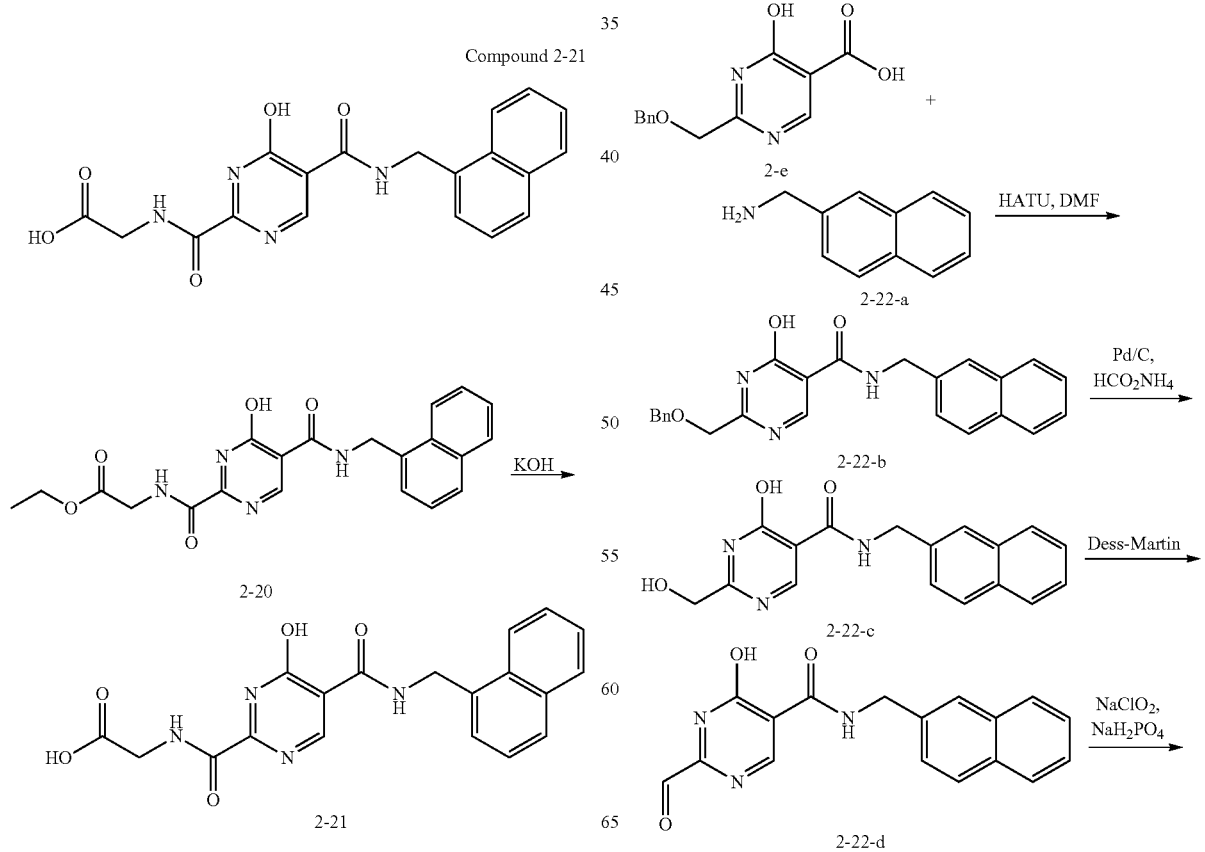

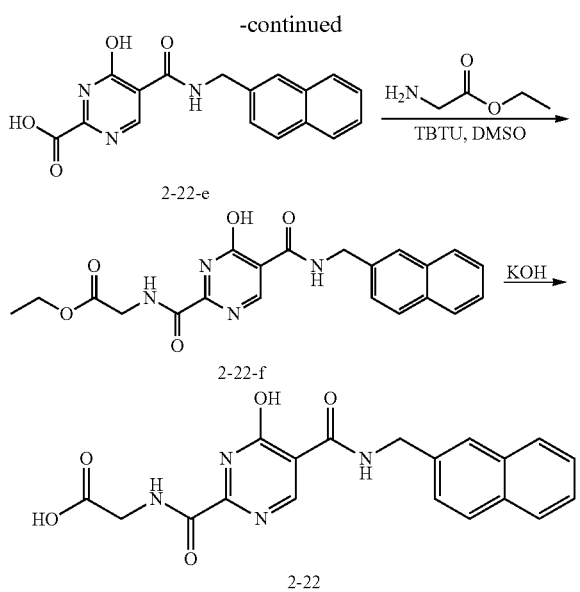

Step A: 2-(benzyloxymethyl)-4-hydroxy-N-(naphthalen-2-ylmethyl)pyrimidine-5-carboxamide (2-22-b)

To a stirred suspension of compound 2-e (5 g, 19.2 mmol) in DMF (50 mL) was added HATU (8.04 g, 21.1 mmol) and EIPEA (2.73 g, 21.1 mmol). The reaction mixture was stirred at ambient temperature until all dissolved. To this stirred solution was added compound 2-22-a (3.17 g, 20.2 mmol) in DMF (20 mL) via syringe. The solution was stirred at room temperature overnight. The reaction mixture was poured into ice-water and extracted with DCM and then concentrated to give a residue. The residue was purified by column chromatography with the eluent DCM:MeOH=60:1 to afford product, 2-22-b, (5.2 g, 68%). $^1$H NMR (300 MHz, CDCl$_3$): δ 9.38 (s, 1H), 8.90 (s, 1H), 7.81-7.75 (m, 4H), 7.43-7.34 (m, 8H), 4.77 (d, J=6.0 Hz, 2H), 4.67 (s, 2H), 4.56 (s, 2H). LC-MS: (M+H)$^+$ 400.

Step B: 4-hydroxy-2-(hydroxymethyl)-N-(naphthalen-2-ylmethyl)pyrimidine-5-carboxamide (2-22-c)

A mixture of step A product, 2-22-b, (4.36 g, 11 mmol), HCOONH$_4$ (1.4 g, 22 mmol) and Pd/C (0.5 g) in EtOH (150 mL) was refluxed overnight. The reaction solution was filtered. The filtration was evaporated under vacuum to obtain a residue, which was purified by column chromatography eluting with DCM:MeOH=20:1 to afford product, 2-22-c, (2.35 g, 69%). $^1$H NMR (300 MHz, DMSO-d$_6$): 8.58 (s, 1H), 7.91-7.8 (m, 4H), 7.51-7.45 (m, 3H), 4.68 (d, J=6.0 Hz, 2H), 4.43 (d, J=6.0 Hz, 2H). LC-MS: (M+H)$^+$ 310.

Step C: 2-formyl-4-hydroxy-N-(naphthalen-2-ylmethyl)pyrimidine-5-carboxamide (2-20-d)

A mixture of step B product (3.0 g, 9.71 mmol) and Dess-Martin reagent (4.94 g, 11.65 mmol) in DCM (50 mL) was stirred at the ambient temperature for 1 h. The reaction solution was evaporated under vacuum to give a residue, which was purified by column chromatography with the eluent DCM:MeOH=60:1-30:1 to afford the crude product (1.8 g,) as a pale solid, 2-20-d.

Step D: 4-hydroxy-5-(naphthalen-2-ylmethylcarbamoyl)pyrimidine-2-carboxylic acid (2-20-e)

To a solution of step C product, 2-20-d, (1.8 g, 5.86 mmol) in t-BuOH (20 mL) was added NaH$_2$PO$_4$.12H$_2$O (1.68 g, 4.69 mmol) followed by H$_2$O (5 mL) and NaClO$_2$ (1.59 g, 17.58 mmol). After being allowed to stir at the ambient temperature for 4 h, the reaction mixture was filtered and collected the filtrate cake to obtain a crude product (2.5 g), which was directly used to the next step without further purification, 2-20-e. LC-MS: (M–H)$^-$ 322.

Step E: 2-(4-hydroxy-5-(naphthalen-1-ylmethylcarbamoyl)pyrimidine-2-carboxamido) acetic acid (2-20-f)

A mixture of step D product, 2-20-e, (2.5 g, 7.7 mmol), ethyl 2-aminoacetate hydrochloride (1.30 g, 9.3 mmol), TBTU (2.98 g, 9.3 mmol), DIPEA (2.99 g, 23.2 mmol) in DMSO (20 mL) and stirred at the ambient temperature overnight. Then the reaction mixture was added ice-water (40 mL), extracted with DCM (30 mL×2). The organic phase was concentrated and purified by column chromatography with DCM:MeOH=150:1 to give crude product, which was purified by pre-HPLC to obtain the solution of compound 2-22-f. This solution was concentrated to remove organic solvent and then directly used to the next step.

Step F: N-({4-hydroxy-5-[(naphthalen-2-ylmethyl)carbamoyl]pyrimidin-2-yl}carbonyl)glycine To the above solution of compound 2-22-f was added KOH (137 mg, 2.5 mmol) and stirred at 50° C. for 30 min. The reaction mixture was extracted with ethyl acetate (20 mL). The aqueous layer was adjusted to pH 2 by addition of HCl. The solids were filtered to afford 2-22 as a white solid (25 mg). $^1$H NMR (300 MHz, DMSO-d$_6$): δ 10.28 (m, 1H), 9.21 (m, 1H), 8.57 (s, 1H), 7.88-7.78 (m, 4H), 7.48-7.45 (m, 3H), 4.70 (s, 2H), 3.92-3.94 (d, 6.0 Hz, 2H). LC-MS: (M+H)$^+$ 381.

Example 3

Synthesis of Intermediate 3-h

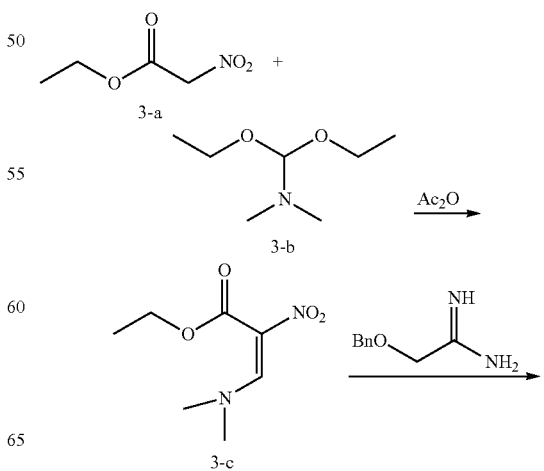

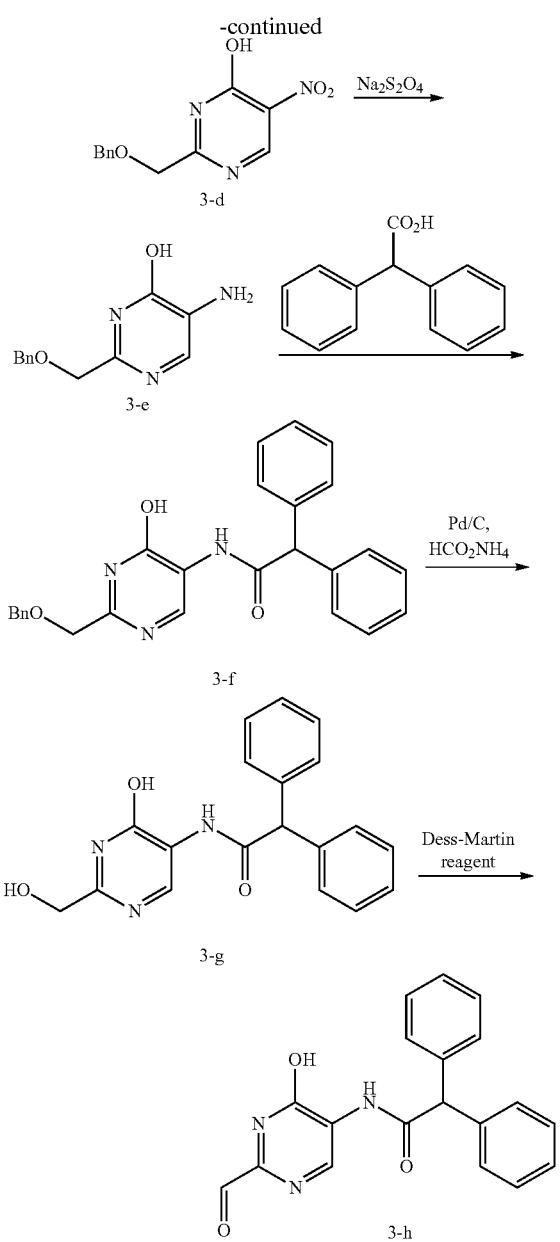

Step C: 5-amino-2-(benzyloxymethyl)pyrimidin-4-ol (3-e)

To a solution of step B product, 3-d, (25 g, crude) in THF/$H_2O$ (1000 mL, $V_{THF/VH2O}$=1:1) was added with $Na_2S_2O_4$ (33.3 g, 191.6 mmol) and stirred at room temperature for 4 h. The reaction mixture was extracted with EA (1000 mL), washed with brine (200 mL), and concentrated in vacuum. The residue was purified by column chromatography to afford the product, 3-e, (7.8 g) as a white solid. $^1$H NMR (300 MHz, CDCl$_3$): δ 4.42 (s, 2H), 4.63 (s, 2H), 7.33-7.36 (m, 6H). LC-MS (M+H)$^+$ 232.1

Step D: N-(2-(benzyloxymethyl)-4-hydroxypyrimidin-5-yl)-2,2-diphenylacetamide (3-f)

A mixture of compound 3-e (1.6 g, 6.9 mmol), 2,2-diphenylacetic acid (1.47 g, 6.9 mmol), DIEA (1.8 g, 13.8 mmol), and TBTU (2.7 g, 8.28 mmol) in DMF (20 mL) was stirred at room temperature overnight. The reaction mixture was added with sat. NH$_4$Cl (50 mL), extracted with DCM (100 mL), washed with water (50 mL) and brine ((50 mL). The organic layer was concentrated and purified by column chromatography to afford the product as a white solid, 3-f (2.2 g, 76%). $^1$H NMR (300 MHz, CDCl$_3$) δ 4.45 (s, 2H), 4.63 (s, 2H), 5.07 (s, 1H), 7.27-7.40 (m, 16H), LC-MS (M+H)$^+$ 426.1

Step E: N-(4-hydroxy-2-(hydroxymethyl)pyrimidin-5-yl)-2,2-diphenylacetamide (3-g)

To a solution of step D product, 3-f, (1.2 g, 2.8 mmol) in MeOH (100 mL) was added Pd/C (200 mg, 10%) and HCO$_2$NH$_4$ (0.36 g, 5.6 mmol). The mixture was stirred and refluxed for 5 h. The reaction mixture was filtered. The liquids were concentrated and purified by column chromatography to afford the product, 3-g (590 mg, 64%). $^1$H NMR (300 MHz, DMSO) δ 4.30 (d, J=4.2 Hz, 2H), 5.66 (s, 1H), 7.21-7.35 (m, 11H), 8.66 (s, 1H), 9.64 (s, 1H). LC-MS (M+H)$^+$ 326.1.

Step F: N-(2-formyl-4-hydroxypyrimidin-5-yl)-2,2-diphenylacetamide (3-h)

To a solution of compound step E product, 3-g, (1.1 g, 3.2 mmol) in DCM was added slowly Dess-Martin reagent (1.6 g, 3.84 mmol) and stirred at room temperature for 20 min. The reaction mixture was concentrated and purified by column chromatography to afford the product, 3-h (1.0 g, 90%). LC-MS (M+H+$H_2O$)$^+$ 352.1.

Step A: Ethyl 3-(dimethylamino)-2-nitroacrylate (3-c)

A mixture of compound 3-a (20 mL, 179 mmol), 3-b (48 mL, 359 mmol) and Ac$_2$O was stirred at room temperature for 2 h, and then stirred at 100° C. for 3 h. The reaction mixture was concentrated in vacuum to afford the crude dark orange liquids (3-c, 40 g). LC-MS (M+H)$^+$ 189.1.

Step B: 2-(Benzyloxymethyl)-5-nitropyrimidin-4-ol (3-d)

To a mixture of step A product, 3-c, (24 g, 127 mmol) and 2-(benzyloxy)acetimidamide (25.9 g, 127 mmol) in CH$_3$OH (30 mL) was added with NaOCH$_3$ (14.2 g, 254 mmol) and 30° C. overnight. The pH of reaction mixture was adjusted to 7 by addition of concentrated HCl. The solids were filtered to afford the crude product, 3-d, (25 g). LC-MS (M+H)$^+$ 262.1

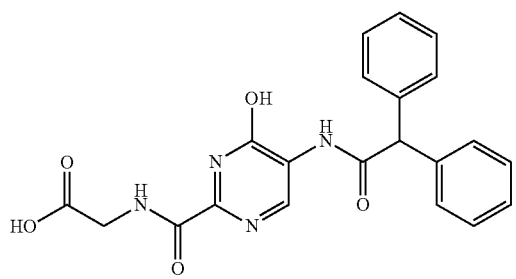

Compound 3-1

2-(5-(2,2-Diphenylacetamido)-4-hydroxypyrimidine-2-carboxamido)acetic acid (3-1) Synthesis of 3-1

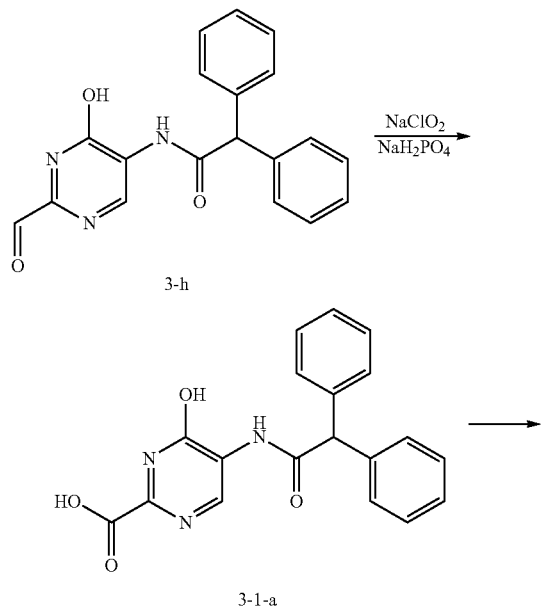

Step A: 5-(2,2-diphenylacetamido)-4-hydroxypyrimidine-2-carboxylic acid (3-1-a)

A mixture of compound 3-h (1 g, 3.0 mmol) in t-BuOH (20 mL) was added to a solution of NaH$_2$PO$_4$·H$_2$O (0.86 g, 2.4 mmol) in H$_2$O (4 mL) and NaClO$_2$ (0.8 g, 9 mmol). After being allowed to stir at room temperature for 3 h, the reaction mixture was added to aq. KOH (2M, 15 mL) and extracted with EA (30 mL). The aqueous layer was adjusted to pH=2 by addition of HCl, and then extracted with EA (30 mL) to afford the crude product, 3-1-a, (300 mg). LC-MS (M+H)$^+$ 350.1

Step B: Methyl 2-(5-(2,2-diphenylacetamido)-4-hydroxypyrimidine-2-carboxamido)acetate (3-1-b)

A mixture of Step A product, 3-1-a, (300 mg, 0.86 mmol), methyl 2-aminoacetate (129 mg, 1.03 mmol) and DIEA (222 mg, 1.7 mmol) in DMSO (10 mL) was added with TBTU (330 mg, 1.03 mmol) and stirred at room temperature for overnight. The reaction mixture was poured into ice water (100 mL). The solids were filtered and purified by pre-HPLC to afford the product as a white solid, 3-1-b, (60 mg, 17%). LC-MS (M+H)$^+$ 421.0

Step C: 2-(5-(2,2-Diphenylacetamido)-4-hydroxypyrimidine-2-carboxamido)acetic acid To a solution of step B, 3-1-b, product (60 mg, 0.143 mmol) in H$_2$O (15 mL) was added KOH (0.2 g, 3.57 mmol) and stirred at 50° C. for 30 min. The reaction mixture was extracted with EA (20 mL). The aqueous layer was adjusted to pH=4 by addition of concentrated HCl. The solids were filtered to afford the product 3-1 as a white solid (15 mg, 25%). NMR (300 MHz, DMSO) δ 3.88 (d, J=6.0 Hz, 2H), 5.75 (s, 1H), 7.14-7.34 (m, 11H), 8.81 (s, 1H), 9.17 (s, 1H), 9.92 (s, 1H), 12.8 (s, 1H). LC-MS (M+H)$^+$ 407.1

Example 3-2

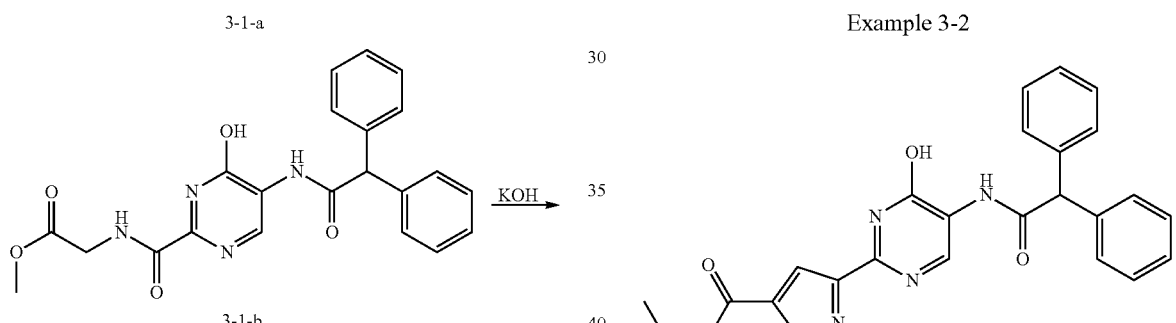

Ethyl 3-(5-(2,2-diphenylacetamido)-4-hydroxypyrimidin-2-yl)isoxazole-5-carboxylate (3-2) Synthesis of 3-2

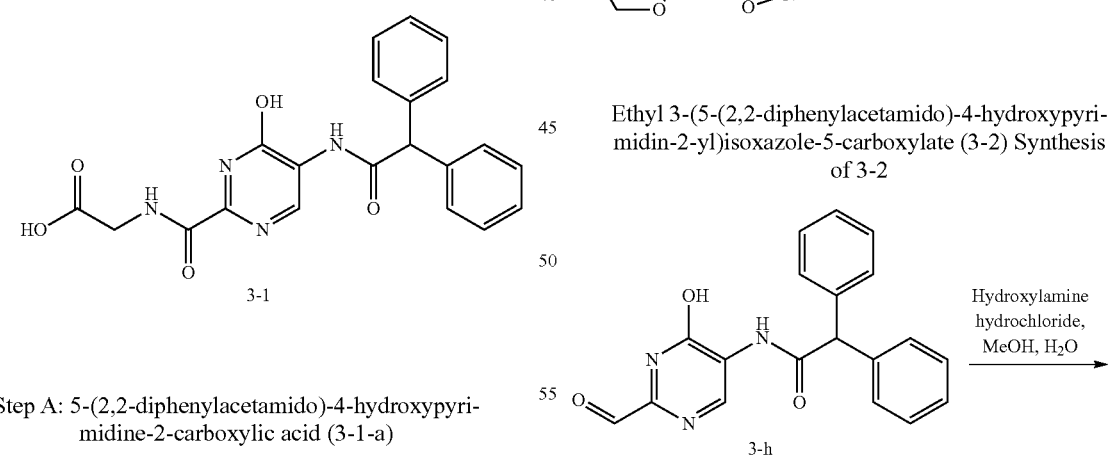

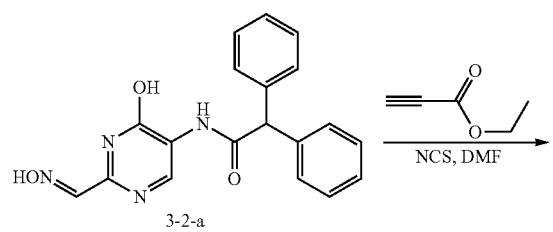

-continued

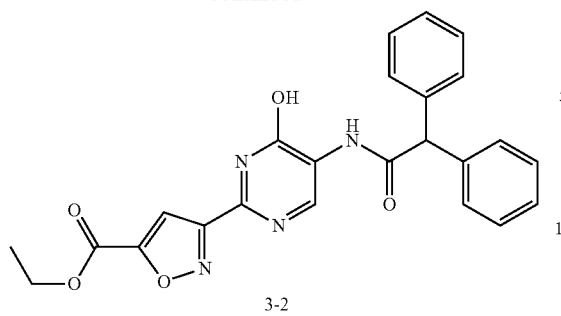

Step A: N-(4-hydroxy-2-((hydroxyimino)methyl)pyrimidin-5-yl)-2,2-diphenyl acetamide (3-2-a)

A mixture of compound 3-h (1 g, 3.0 mmol), NaOAc (0.5 g, 6.0 mmol) and hydroxyamine hydrochloride (0.31 g, 4.5 mmol) in H$_2$O (25 mL) was stirred at 100° C. for 2 h. The precipitated was isolated by filtration to afford the product, 3-2-a, as a white solid. $^1$H NMR (300 MHz, DMSO-d$_6$): δ 12.31 (s, 1H), 9.89 (s, 1H), 8.85 (s, 1H), 7.74 (s, 1H), 7.33-7.23 (m, 1H), 5.71 (s, 1H). LC-MS: (M+H)$^+$ 349.

Step B: Ethyl 3-(5-(2,2-diphenylacetamido)-4-hydroxypyrimidin-2-yl)isoxazole-5-carboxylate (3-2)

To a solution of step A product, 3-2-a, (0.85 g, 2.4 mmol) in DMF (15 mL), was added NCS (0.42 g, 3.15 mmol) at room temperature. The reaction mixture was heated at 60° C. for 1 h. The reaction mixture was cooled to 0° C. and ethyl propiolate (0.67 g, 6.8 mmol) was added. Then Et$_3$N (0.3 g, 3 mmol) in DMF (5 mL) was added dropwise over 20 min. The reaction mixture was slowly allowed to warm to room temperature and stirred for overnight. The mixture was diluted with water (50 mL) and extracted with EA (100 mL). The organic layer was washed with brine (50 mL), dried over Na$_2$SO$_4$, and concentrated in vacuum. The residue was purified by column chromatography with the eluent (PE:EA=2:1) to afford 3-2 (150 mg, 14%) as a light yellow solid. $^1$H NMR (300 MHz, DMSO-d$_6$) δ10.04 (s, 1H), 8.9 (s, 1H), 7.68 (s, 1H), 7.35-7.26 (m, 11H), 5.76 (s, 1H), 4.40 (q, J=7.2 Hz, 2H), 1.34 (t, J=7.2 Hz, 3H). LC-MS: (M+H)$^+$ 445.

Compound 3-3

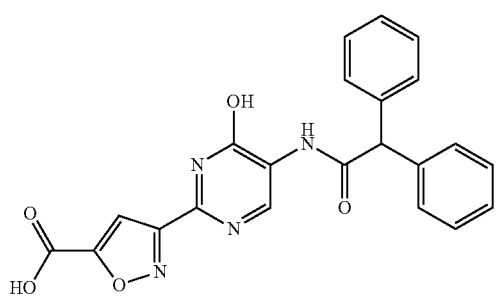

(5-(2,2-diphenylacetamido)-4-hydroxypyrimidin-2-yl)isoxazole-5-carboxylic acid (3-3)

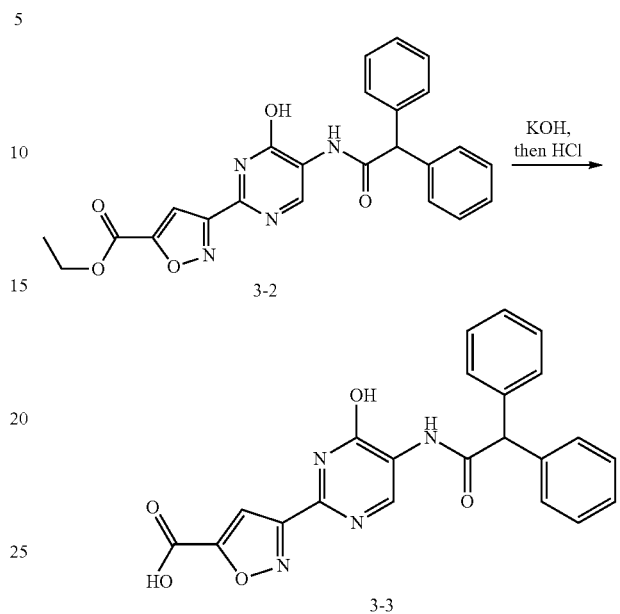

To a suspension of compound 3-2 (60 mg, 0.135 mmol) in H$_2$O (100 mL) was added KOH (75 mg, 1.35 mmol) and stirred at 50° C. for 30 min. The reaction mixture was extracted with EA (20 mL). The aqueous layer was adjusted to pH 3 by addition of HCl. The solids were filtered to afford compound 3-3 as a white solid (40 mg, 71%). $^1$H NMR (300 MHz, DMSO-d$_6$) δ 13.61 (br s, 1H), 10.02 (s, 1H), 8.99 (s, 1H), 7.35-7.26 (m, 12H), 5.76 (s, 1H). LC-MS: (M+H)$^+$ 417.

Biological Assays

The exemplified compounds, Examples 1 through 13 of the present invention, have been found to inhibit the interaction between PHD2 and a HIF peptide and exhibit IC$_{50}$ values ranging between 0.1 nanomolar to 10 micromolar. Non-limiting examples of assays that may be useful to detect favorable activity are disclosed in the following publications: Oehme, F., et al., *Anal. Biochem.* 330:74-80 (2004); Hirsild, M, et al., *J. Bio. Chem.* 278 (33): 30772-30780 (2005); Hyunju, C., et al., *Biochem. Biophys. Res. Comm.* 330 (2005) 275-280; and Hewitson, K. S., et al., *Methods in Enzymology*, (Oxygen Biology and Hypoxia); Elsevier Publisher (2007), pg. 25-42 (ISSN: 0076-6879).

The biological activity of the present compounds may be evaluated using assays described herein below:

To each well of a 96-well plate was added 1 μL of test compound in DMSO and 20 μl of assay buffer (50 mM Tris pH 7.4/0.01% Tween-20/0.1 mg/ml bovine serum albumin/10 μM ferrous sulfate/1 mM sodium ascorbate/20 μg/ml catalase) containing 0.15 μg/ml FLAG-tagged full length PHD2 expressed in and purified from baculovirus-infected Sf9 cells. After a 30 min preincubation at room temperature, the enzymatic reactions were initiated by the addition of 4 μL of substrates (final concentrations of 0.2 μM 2-oxoglutarate and 0.5 μM HIF-1α peptide biotinyl-DLDLEMLAPYIPMD-DDFQL (SEQ ID NO:1)). After 2 hours at room temperature, the reactions were terminated and signals were developed by the addition of a 25 μL quench/detection mix to a final concentration of 1 mM ortho-phenanthroline, 0.1 mM EDTA, 0.5 nM anti-(His)$_6$ LANCE reagent (Perkin-Elmer Life Sciences), 100 nM AF647-labeled streptavidin (Invitrogen), and 2 µg/ml (His)$_6$-VHL complex (S. Tan (2001) Protein Expr. Purif. 21, 224-234). The ratio of time resolved fluorescence signals at 665 and 620 nm was determined; and percent inhibition was calculated relative to an uninhibited control sample run in parallel.

Inhibition of the catalytic activity of HIF-PHD1 and HIF-PHD3 can be determined similarly.

Table 6 depicts the inhibition of HIF PHD2 activity expressed as IC$_{50}$ (nM), for the exemplified compounds of the present invention.

TABLE 6

PHD2 Inhibition Activity

| Cmp. No. | Compound IUPAC name | IC$_{50}$ (nM) |
| --- | --- | --- |
| 1-1 | 1-(5-(benzhydrylcarbamoyl)-4-hydroxypyrimidin-2-yl)-1H-pyrazol-4-yl(methyl) phosphinic acid | + |
| 2-1 | Ethyl N-({5-[(diphenylmethyl)carbamoyl]-4-hydroxypyrimidin-2-yl}carbonyl)-β-alaninate | + |
| 2-2 | Ethyl N-({5-[(diphenylmethyl)carbamoyl]-4-hydroxypyrimidin-2-yl}carbonyl)glycinate | + |
| 2-3 | Methyl N-({5-[(diphenylmethyl)carbamoyl]-4-hydroxypyrimidin-2-yl}carbonyl)glycinate | + |
| 2-4 | 2-[({5-[(diphenylmethyl)carbamoyl]-4-hydroxypyrimidin-2-yl}carbonyl)amino]ethanesulfonic acid | + |
| 2-5 | Diethyl {[({5-[(diphenylmethyl)carbamoyl]-4-hydroxypyrimidin-2-yl}carbonyl)amino]methyl}phosphonate | ++ |
| 2-6 | Ethyl {[({5-[(diphenylmethyl)carbamoyl]-4-hydroxypyrimidin-2-yl}carbonyl)amino]methyl}methylphosphinate | + |
| 2-7 | Benzyl N-({5-[(diphenylmethyl)carbamoyl]-4-hydroxypyrimidin-2-yl}carbonyl)glycinate | + |
| 2-11 | 3-(5-(benzhydrylcarbamoyl)-4-hydroxypyrimidine-2-carboxamido)propanoic acid | + |
| 2-12 | 2-(5-(benzhydrylcarbamoyl)-4-hydroxypyrimidine-2-carboxamido)acetic acid | + |
| 2-13 | {[({5-[(diphenylmethyl)carbamoyl]-4-hydroxypyrimidin-2-yl}carbonyl)amino]methyl}phosphonic acid | ++ |
| 2-14 | {[({5-[(diphenylmethyl)carbamoyl]-4-hydroxypyrimidin-2-yl}carbonyl)amino]methyl}methylphosphinicacid | + |
| 2-17 | 2-(5-(bis(4-methoxyphenyl)methylcarbamoyl)-4-hydroxypyrimidine-2-carboxamido)acetic acid | + |
| 2-18 | Ethyl-2-(5-(bis(4-fluorophenyl)methylcarbamoyl)-4-hydroxypyrimidine-2-carboxamido)acetate | + |
| 2-19 | 2-(5-(bis(4-fluorophenyl)methylcarbamoyl)-4-hydroxypyrimidine-2-carboxamido) acetic acid | + |
| 2-20 | Ethyl-2-(4-hydroxy-5-(naphthalen-1-ylmethylcarbamoyl)pyrimidine-2-carboxamido)acetate | +++ |
| 2-21 | 2-(4-hydroxy-5-(naphthalen-1-ylmethylcarbamoyl)pyrimidine-2-carboxamido)aceticacid | ++ |
| 2-22 | N-({4-hydroxy-5-[(naphthalen-2-ylmethyl)carbamoyl]pyrimidin-2-yl}carbonyl)glycine | ++ |
| 3-1 | 2-(5-(2,2-Diphenylacetamido)-4-hydroxypyrimidine-2-carboxamido)acetic acid | + |

+ = 0.5 ≤ IC$_{50}$ ≤ 20 (nM)
++ = 20 < IC$_{50}$ ≤ 100 (nM)
+++ = 100 < IC$_{50}$ ≤ 10000(nM)

What is claimed is:

1. A compound of formula I and pharmaceutically acceptable salts and solvates thereof

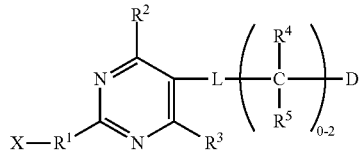

R$^1$ is —CONR$^a$(C$_{1-2}$)alkyl-, a heteroarylene selected from isoxazoldiyl, pyrazoldiyl, imidazoldiyl, oxazoldiyl, thiazoldiyl, pyridindiyl, pyradizindiyl, and pyrimidindiyl;

R$^2$, R$^3$, and R$^6$ are each independently selected from hydrogen, hydroxy, and C$_{1-6}$ alkyl;

X is selected from —COOR, —PO(R')OR, —PO(OR)$_2$, —PO(NRR)$_2$, —SO$_3$R, —PO(C$_{1-10}$alkyl)OR, PO(C$_{3-10}$cycloalkyl)OR, PO(H)OR, and PO(NHCR'R''COOR)$_2$ R is independently selected from hydrogen, C$_{1-10}$ alkyl, —C$_{1-5}$ alkylaryl, —CR'R—OCO—C$_{1-10}$ alkyl, and —CR'R'—OCO—OC$_{1-10}$ alkyl;

R' and R'' are independently selected from hydrogen and C$_{1-10}$ alkyl;

L is selected from —CONR$_6$—, and —NR$_6$CO—;

D is selected from hydrogen, aryl and heteroaryl;

R$^a$, R$^4$, and R$^5$ are each independently selected from
 hydrogen,
 halogen,
 caboxyl C$_{0-10}$ alkyl,
 C$_{1-10}$ alkyl,
 C$_{2-10}$ alkenyl,
 C$_{2-10}$ alkynyl,
 C$_{1-10}$ alkenylamino,
 C$_{1-10}$ alkyl(oxy)$_{0-1}$ carbonylC$_{1-10}$ alkyl,
 aryl C$_{0-10}$ alkyl(oxy)$_{0-1}$ carbonylC$_{1-10}$ alkyl,
 C$_{3-8}$ cycloalkyl C$_{0-10}$ alkyl(oxy)$_{0-1}$carbonyl C$_{1-10}$ alkyl,
 (C$_{3-8}$)heterocyclyl C$_{0-10}$ alkyl(oxy)$_{0-1}$carbonyl C$_{1-10}$ alkyl,
 (C$_{3-8}$)heterocycloalkyl C$_{0-10}$ alkyl(oxy)$_{0-1}$ carbonyl C$_{1-10}$ alkyl,
 arylC$_{0-10}$alkyl,
 C$_{3-8}$ cycloalkyl C$_{0-10}$ alkyl,
 C$_{3-8}$ heterocyclyl C$_{0-10}$ alkyl,
 C$_{3-8}$ heterocycloalkyl C$_{0-10}$ alkyl,
 C$_{1-10}$ alkoxyl, and
 hydroxy C$_{0-10}$alkyl;
wherein, R$^1$, R$^a$, R$^4$, R$^5$, and D are optionally substituted with 1, 2, or 3 substituent R$^7$, selected from:
 halogen,
 (carbonyl)$_{0-1}$C$_{1-10}$ alkyl,
 (carbonyl)$_{0-1}$ C$_{2-10}$ alkenyl,
 (carbonyl)$_{0-1}$ C$_{2-10}$alkynyl,
 C$_{1-10}$ alkylcarbonyl,
 C$_{2-10}$ alkenylcarbonyl,
 C$_{2-10}$ alkynylcarbonyl,
 arylC$_{0-10}$ alkyl,
 (C$_{3-8}$)heterocyclyl C$_{0-10}$ alkyl,
 C$_{3-8}$ cycloalkyl C$_{0-10}$ alkyl,
 (C$_{3-8}$)heterocycloalkyl C$_{0-10}$ alkyl,
 C$_{1-4}$acylamino C$_{0-10}$ alkyl,
 C$_{0-10}$ alkylamino C$_{0-10}$ alkyl,
 arylC$_{0-10}$ alkylamino C$_{0-10}$ alkyl,
 C$_{3-8}$ cycloalkyl C$_{0-10}$ alkylamino C$_{0-10}$ alkyl,
 C$_{3-8}$ heterocyclyl C$_{0-10}$ alkylamino C$_{0-10}$ alkyl,
 C$_{3-8}$ heterocycloalkyl C$_{0-10}$ alkylamino C$_{0-10}$ alkyl,
 C$_{1-10}$ alkyloxy C$_{0-10}$alkyl,
 (C$_{1-10}$ alkyl)2aminocarbonyloxy,
 hydroxy C$_{0-10}$alkyl,
 C$_{1-10}$ alkylsulfonyl,
 C$_{1-10}$ alkylsulfonylamino,
 aryl C$_{1-10}$ alkylsulfonylamino,
 C$_{3-8}$ heterocyclyl C$_{1-10}$ alkylsulfonylamino,
 C$_{3-8}$ heterocycloalkyl C$_{1-10}$ alkylsulfonylamino,
 C$_{3-8}$ cycloalkyl C$_{1-10}$ alkylsulfonylamino,
 cyano,
 nitro,
 perfluoroC$_{1-6}$alkyl, and
 perfluoroC$_{1-6}$alkoxy;
wherein R$^7$ is optionally substituted with 1, 2, or 3 substituents selected from hydrogen, hydroxy, (C$_{1-6}$)alkoxyl, halogen, CO$_2$H, CN, O(C=O)C$_1$-C$_6$ alkyl, NO$_2$, trifluoromethoxy, trifluoroethoxy, —O$_{(0-1)}$(C$_{1-10}$)perfluoroalkyl, and NH$_2$; and
provided that when R$^1$ is a heteroarylene, then X is other than —COOR.

2. A compound of claim 1 wherein R$^1$ is —CONR$^a$(C$_{1-2}$) alkyl-, optionally substituted with 1, 2, or 3 R$^7$ substituents.

3. A compound of claim 1 wherein R$^1$ is a heteroarylene selected from isoxazoldiyl, imidazoldiyl, oxazoldiyl, pyridindiyl, and pyrimidindiyl, optionally substituted with 1, 2, or 3 R$^7$ substituents.

4. A compound of claim 1 wherein R$^2$ is hydroxy.

5. A compound of claim 1 wherein R$^3$ is hydrogen.

6. A compound of claim 1 wherein R$^6$ is hydrogen.

7. A compound of claim 1, wherein R$^a$, R$^4$, and R$^5$ are each independently selected from hydrogen, arylC$_{0-10}$ alkyl, C$_{3-8}$ cycloalkyl C$_{0-10}$ alkyl, C$_{3-8}$ heterocyclyl C$_{0-10}$ alkyl, C$_{3-8}$ heterocycloalkylC$_{0-10}$ alkyl, and hydroxyC$_{0-10}$alkyl; wherein R$^a$, R$^4$, and R$^5$ are each optionally substituted by 1, 2, or 3 R$^7$ substituents.

8. A compound of claim 7, wherein R$^a$, R$^4$, and R$^5$ are selected from: hydrogen, halogen, and C$_{1-10}$ alkyl.

9. A compound of claim 3, wherein R$^1$ is selected from isoxazoldiyl, imidazoldiyl, and oxazoldiyl, optionally substituted with 1, 2, or 3 R$^7$ substituents.

10. A compound of claim 1, wherein substituent R$^7$ is selected from: halogen, (carbonyl)$_{0-1}$C$_{1-10}$ alkyl, aryl C$_{0-10}$ alkyl, (C$_{3-8}$)heterocyclyl C$_{0-10}$ alkyl, C$_{3-8}$ cycloalkyl C$_{0-10}$ alkyl, (C$_{3-8}$)heterocycloalkyl C$_{0-10}$ alkyl, C$_{1-10}$alkyloxy C$_{0-10}$ alkyl, hydroxy C$_{0-10}$alkyl, C$_{1-10}$ alkylsulfonyl, cyano, nitro, perfluoroC$_{1-6}$alkyl, and perfluoroC$_{1-6}$alkoxy.

11. A compound of claim 10, wherein substituent R$^7$ is selected from: halogen, (carbonyl)$_{0-1}$C$_{1-10}$ alkyl, C$_{1-10}$ alkyloxy C$_{0-10}$alkyl, hydroxy C$_{0-10}$alkyl, cyano, nitro, perfluoroC$_{1-6}$ alkyl, and perfluoroC$_{1-6}$ alkoxy.

12. A compound selected from:
 1-(5-(benzhydrylcarbamoyl)-4-hydroxypyrimidin-2-yl)-1H-pyrazol-4-yl(methyl)phosphinic acid;
 Ethyl N-({5-[(diphenylmethyl)carbamoyl]-4-hydroxypyrimidin-2-yl}carbonyl)-β-alaninate;
 Ethyl N-({5-[(diphenylmethyl)carbamoyl]-4-hydroxypyrimidin-2-yl}carbonyl)glycinate;
 Methyl N-({5-[(diphenylmethyl)carbamoyl]-4-hydroxypyrimidin-2-yl}carbonyl)glycinate;
 2-[({5-[(diphenylmethyl)carbamoyl]-4-hydroxypyrimidin-2-yl}carbonyl)amino]ethanesulfonic acid;
 Diethyl {[({5-[(diphenylmethyl)carbamoyl]-4-hydroxypyrimidin-2-yl}carbonyl)amino]methyl}phosphonate;

Ethyl {[({5-[(diphenylmethyl)carbamoyl]-4-hydroxypyrimidin-2-yl}carbonyl)amino]methyl}methylphosphinate;

Benzyl N-({5-[(diphenylmethyl)carbamoyl]-4-hydroxypyrimidin-2-yl}carbonyl)glycinate;

3-(5-(benzhydrylcarbamoyl)-4-hydroxypyrimidine-2-carboxamido)propanoic acid;

2-(5-(benzhydrylcarbamoyl)-4-hydroxypyrimidine-2-carboxamido)acetic acid;

{[({5-[(diphenylmethyl)carbamoyl]-4-hydroxypyrimidin-2-yl}carbonyl)amino]methyl}phosphonic acid;

{[({5-[(diphenylmethyl)carbamoyl]-4-hydroxypyrimidin-2-yl}carbonyl)amino]methyl}methylphosphinic acid;

2-(5-(bis(4-methoxyphenyl)methylcarbamoyl)-4-hydroxypyrimidine-2-carboxamido)acetic acid;

Ethyl-2-(5-(bis(4-fluorophenyl)methylcarbamoyl)-4-hydroxypyrimidine-2-carboxamido)acetate;

2-(5-(bis(4-fluorophenyl)methylcarbamoyl)-4-hydroxypyrimidine-2-carboxamido) acetic acid;

Ethyl-2-(4-hydroxy-5-(naphthalen-1-ylmethylcarbamoyl)pyrimidine-2-carboxamido)acetate;

2-(4-hydroxy-5-(naphthalen-1-ylmethylcarbamoyl)pyrimidine-2-carboxamido)acetic acid;

N-({4-hydroxy-5-[(naphthalen-2-ylmethyl)carbamoyl]pyrimidin-2-yl}carbonyl)glycine;

2-(5-(2,2-Diphenylacetamido)-4-hydroxypyrimidine-2-carboxamido)acetic acid;

and pharmaceutically acceptable salts and solvates thereof.

13. A compound selected from:

2-(5-(bis(4-methoxyphenyl)methylcarbamoyl)-4-hydroxypyrimidine-2-carboxamido)acetic acid;

3-(5-(benzhydrylcarbamoyl)-4-hydroxypyrimidine-2-carboxamido)propanoic acid;

and pharmaceutically acceptable salts and solvates thereof.

14. A pharmaceutical composition comprising a compound of claim 1 and pharmaceutically acceptable carrier.

15. A method for the treatment of anemia in a mammal which comprises administering to the mammal an effective amount of a compound of claim 1, or a pharmaceutically acceptable salt or solvate thereof.

* * * * *